United States Patent [19]

Pearson et al.

[11] Patent Number: 5,406,082
[45] Date of Patent: Apr. 11, 1995

[54] SURFACE INSPECTION AND CHARACTERIZATION SYSTEM AND PROCESS

[75] Inventors: Lee H. Pearson, Bear River City, Utah; John Stover, Bozeman, Mont.; Mary Knighton, Bozeman, Mont.; Brett Swimley, Bozeman, Mont.

[73] Assignee: Thiokol Corporation, Ogden, Utah

[21] Appl. No.: 982,293

[22] Filed: Nov. 27, 1992

Related U.S. Application Data

[63] Continuation-in-part of Ser. No. 873,937, Apr. 24, 1992.

[51] Int. Cl.$^6$ .................... G01N 21/35; G01N 21/47
[52] U.S. Cl. .................. 250/339.01; 250/301; 250/341.1
[58] Field of Search ................. 250/341, 339, 301

[56] References Cited

U.S. PATENT DOCUMENTS

| | | | |
|---|---|---|---|
| 2,404,064 | 7/1946 | Heigl et al. | 250/339 |
| 2,516,672 | 7/1950 | Brockman | 338/18 |
| 2,562,525 | 7/1951 | Cary | 250/339 |
| 2,634,908 | 4/1953 | Jackson, Jr. et al. | 364/856 |
| 2,650,307 | 8/1953 | Koppius | 250/339 |
| 2,706,253 | 4/1955 | Hutchins et al. | 250/339 |
| 2,775,160 | 12/1956 | Foskett et al. | 356/418 |
| 2,897,371 | 7/1959 | Hasler | 378/50 |
| 3,017,512 | 1/1962 | Wolbert | 250/349 |
| 3,048,699 | 8/1962 | Francis | 250/338.1 |
| 3,153,722 | 10/1964 | Bayly et al. | 250/339 |
| 3,373,281 | 3/1968 | McAlister | 250/253 |
| 3,433,052 | 3/1969 | Maley | 374/5 |
| 3,451,254 | 6/1969 | Maley | 374/5 |
| 3,457,412 | 7/1969 | Cary | 250/351 |
| 3,471,698 | 10/1969 | Mausteller et al. | 250/351 |
| 3,603,952 | 9/1971 | Smith | 340/539 |
| 3,653,765 | 4/1972 | Hearn | 356/306 |
| 3,661,462 | 5/1972 | Natens | 356/51 |
| 3,675,019 | 7/1972 | Hill et al. | 250/350 |
| 3,693,025 | 9/1972 | Brunton | 250/340 |
| 3,700,898 | 10/1972 | MacLeod | 250/343 |
| 3,734,621 | 5/1973 | Moody et al. | 356/325 |
| 3,747,755 | 7/1973 | Senturia et al. | 209/111.5 |
| 3,783,284 | 1/1974 | McCormack | 250/339 |
| 3,803,414 | 4/1974 | Van Horne et al. | 250/339 |
| 3,904,880 | 9/1975 | Benz et al. | 250/343 |
| 3,994,586 | 11/1976 | Sharkins et al. | 356/73 |
| 4,015,127 | 3/1977 | Sharkins | 250/341 |
| 4,085,326 | 4/1978 | Williams | 250/339 |
| 4,274,091 | 6/1981 | Decker | 340/583 |
| 4,320,967 | 3/1982 | Edgar | 356/51 |
| 4,345,150 | 8/1982 | Tamura et al. | 250/339 |
| 4,363,966 | 12/1982 | Cheo | 250/339 |
| 4,406,545 | 9/1983 | Montone et al. | 356/380 |
| 4,410,273 | 10/1983 | Mantz et al. | 356/319 |
| 4,427,889 | 1/1984 | Müller | 250/339 |
| 4,433,239 | 2/1984 | Thompson | 250/255 |
| 4,490,845 | 12/1984 | Steinbrugge et al. | 382/1 |
| 4,527,062 | 7/1985 | Novinson | 250/351 |
| 4,590,574 | 5/1986 | Edmonds et al. | 364/498 |
| 4,602,342 | 7/1986 | Gottlieb et al. | 364/498 |

(List continued on next page.)

FOREIGN PATENT DOCUMENTS 3-115838  5/1991  Japan .

OTHER PUBLICATIONS

E. Neil Lewis et al., "A Miniaturized, No-Moving-Parts Raman Spectrometer," *Applied Spectroscopy*, vol. 47, No. 5, pp. 539–543 (1993).

(List continued on next page.)

*Primary Examiner*—Constantine Hannaher
*Attorney, Agent, or Firm*—Madson & Metcalf; Ronald L. Lyons

[57] ABSTRACT

A system and process for obtaining near real time, non-destructive inspection and characterization of surfaces. The system includes an infrared light source which is directed on a surface to be inspected. A portion of the reflected light is gathered and directed through an optical filter arrangement which separates the light into a plurality of sets of wavelengths which correspond to particular physical properties of the thin film, such as absorbance. The intensity of each set of wavelengths is detected by optical detectors and the resulting signals analyzed to characterize the surface.

39 Claims, 3 Drawing Sheets

U.S. PATENT DOCUMENTS

| | | | |
|---|---|---|---|
| 4,616,134 | 10/1986 | Pruett et al. | 250/255 |
| 4,622,845 | 11/1986 | Ryan et al. | 73/24 |
| 4,652,756 | 3/1987 | Ryan et al. | 250/343 |
| 4,653,908 | 3/1987 | Yajima et al. | 356/51 |
| 4,663,961 | 5/1987 | Nelson et al. | 73/24 |
| 4,677,298 | 6/1987 | Zelmanovic et al. | 250/341 |
| 4,690,553 | 9/1987 | Fukamizu et al. | 356/51 |
| 4,718,026 | 1/1988 | Long et al. | 364/550 |
| 4,736,103 | 4/1988 | Nelson et al. | 250/343 |
| 4,771,629 | 9/1988 | Carlson et al. | 73/23.1 |
| 4,787,750 | 11/1988 | Nelson et al. | 356/437 |
| 4,808,824 | 2/1989 | Sinnar | 250/339 |
| 4,822,169 | 4/1989 | Distl et al. | 356/364 |
| 4,883,963 | 11/1989 | Kemeny et al. | 250/339 |
| 4,965,452 | 10/1990 | Sturm | 250/339 |
| 5,036,203 | 7/1991 | Solomon | 250/370.06 |
| 5,070,242 | 12/1991 | McClelland et al. | 250/339 |
| 5,120,961 | 6/1992 | Levin et al. | 250/339 |

OTHER PUBLICATIONS

Chieu D. Tran and Ricardo J. Furlan, "Acousto-Optic Tunable Filter as a Polychromator and Its Application in Multidimensional Fluorescence Spectrometry," *Anal. Chem.*, 1992, vol. 64, No. 22, pp. 2775–2782 (Nov. 15, 1992).

Ira Kurtz et al., "Rapid scanning fluorescence spectroscopy using an acousto–optic tunable filter," *Rev. Sci. Instrum.*, vol. 58, No. 11, pp. 1996–2003 (Nov. 1987).

*Acqousto–Optic Products*, Brimrose Corporation, Baltimore, Md. (Jan. 1992).

Pearson, L. H., "Diffuse Reflectance IR Spectroscopy for Bonding Surface Contamination Characterization," *Proceedings of the Review Progress in Quantitative Nondestructive Evaluation*, (Jul. 1990).

Carl, R. T., and Smith, M. J., "Material Analysis by Infrared Microimaging," *Review of Process in Quantitative Nondestructive Evaluation*, (1990).

Pearson, L. H., "IR Spectroscopy for Bonding Surface Contamination Characterization," *Proceedings of the Review of Progress in Quantitative Nondestructive Evaluation* (Aug. 1989).

*DCI 4000 Series Multi Axis Stepping Motor Controller Instruction Manual*, Design Components, Inc. Franklin, Mass. (Aug. 1988).

[Untitled Instructions and Schematics for Positioning Table], Design Components, Inc., Franklin, Mass. (date unknown).

*Nicolet IR Microspectroscopy* [advertisement], Nicolet Corporation, Madison, Wis. (date unknown).

Hunt, J. H., "Surfs (Surface Spectroscopy)," Rockwell International, Rocketdyne Division (date unknown).

SURFACE INSPECTION AND CHARACTERIZATION SYSTEM AND PROCESS

RELATED U.S. APPLICATION

This application is a continuation in part of application Ser. No. 07/873,937 filed Apr. 24, 1992 and entitled INFRARED REFLECTANCE ACOUSTO-OPTIC TUNABLE FILTER SPECTROMETER-BASED SURFACE SCANNING SYSTEM AND PROCESS.

BACKGROUND

1. The Field of the Invention

The present invention is related to a system and process for inspecting and characterizing surfaces. More particularly, the present invention is related to a system and process for obtaining near real time, non-destructive inspection and characterization of thin films, particularly organic contaminants, utilizing optical filters and an array of detectors to analyze the spectral content of infrared light reflected off the surface.

2. Technical Background

A typical manufacturing process utilized in many applications is the bonding together of two materials. The criticality of the strength of the bond will vary depending on the particular application for which the bonded material is to be used.

A weak bond or area of debonding can be the source of stress risers which can result in further weakening of the bond. Eventually, these stress risers can lead to failure of the bond and can distort the geometry of the bonded material thereby adversely affecting the performance characteristics of the part.

When two materials are bonded together, contaminants on the surface of either of the materials can weaken the bond and, in some instances, cause areas of debonding. Organic materials such as greases, hydraulic fluids and mold release agents are a primary source of contamination of bonding surfaces in many production applications. Other contaminants which are frequently present in manufacturing environments include particulates such as sand or dust. Oil vapors are often present in environments where hydraulic systems and electric motors are operated. These vapors can condense on surfaces to be bonded. Even small levels of these contaminants, not visible to the human eye, can degrade bond strength.

The extent to which a surface can be cleaned prior to bonding and the method to be utilized in cleaning the surface vary according to the nature of the surface. For example, large-area, grit-blasted steel surfaces may be cleaned by a vapor degrease process. According to one such cleaning process, the part including the surface to be cleaned is suspended within a pit in the bottom of which boiling methylchloroform is located. The methylchloroform evaporates and condenses on the surface. As it runs off the surface, it dissolves any grease in its path. While this process works well in cleaning small amounts of grease from a grit-blasted metal surface, if there are areas of localized buildup of grease, not all of the grease may be removed by the cleaning process.

Using a solvent such as methylchloroform to clean a bonding surface may not be viable if the bonding surface is a porous material such as a phenolic. Phenolic materials will absorb virtually any type of cleaning solvent with which they come into contact. Contact with cleaning solvents can alter the surface chemistry and/or carry dissolved contaminants into the phenolic. In many applications involving phenolics, the surface properties of the phenolics must remain unchanged.

Presently, the preferred method of cleaning a phenolic material is to place it on the mill and machine a new surface, thereby removing the contaminated surface. However, this can only be done if the tolerances of the part permit a portion of the surface to be removed. Otherwise, a contaminated part may have to be replaced.

Because even small levels of contaminants, not visible to the human eye, can degrade bond strength, bonding surfaces must be inspected prior to bonding to ensure that there is no contamination, or that if there is contamination, it is within acceptable limits. Thus, an ideal surface inspection will reveal whether contamination exists, identify the contamination and measure the thickness of the contamination.

A crude method of conducting a surface inspection is to place some solvent on a wipe and stroke the surface with the wipe thereby transferring surface contaminants to the wipe. The wipe may then be analyzed using standard spectroscopy methods to verify the existence of contaminants on the wipe and determine their identity.

A principal obstacle to the successful use of this method is that it can only be used as a check method. It cannot be effectively used as an inspection method over a large-area surface. And, while the method may provide information about the existence of a contaminant and its identity, it cannot be used to provide any quantitative information concerning the thickness of the contamination. It is merely a qualitative method. Additionally, this method cannot be used with phenolic materials because the surface chemistry of the phenolics would be altered by bringing the surface into contact with a wipe permeated with solvent.

A more versatile surface inspection method is to conduct a visual inspection with the aid of an ultraviolet light. Some contaminants, particularly grease such as that used for rust protection, fluoresce under ultraviolet light. Thus, by visually inspecting the surface under ultraviolet light, any contaminants which fluoresce under the light can readily be detected.

The disadvantage of this method is that the method provides no information about the thickness of the contamination. Additionally, this method cannot be used to detect low levels of contamination as it is limited by what can be seen with the human eye. While attempts to instrument this method have been made, such an instrumented approach is prohibitively expensive for most applications. Also, depending on the nature of the potential contamination, contaminant detection may be frustrated as some contaminants do not fluoresce when illuminated with ultraviolet light.

Alternative inspection methods include an optically stimulated electron emission ("OSEE") method. The OSEE method is based on the photoelectric effect. By shining ultraviolet light on the surface to be inspected, electrons are emitted from the surface. By placing an electrode near the surface and raising the electrode to a predetermined voltage, an electric field is generated, drawing an electron current from the surface whose strength can be monitored. If there is contamination on the surface, the current is generally impeded.

A disadvantage to the OSEE method is that it is subject to many variables which are not relevant to the determination of contamination. Such variables may include air currents surrounding the device being tested, relative humidity and moisture on the surface. Also, the OSEE method only works effectively on metals. It is ineffective as a tool to inspect phenolic, rubber or oxidized metal surfaces.

Other optical methods have also been proposed. However, they are generally ineffective for the inspection of large-area surfaces because of the amount of time required to obtain and process a sufficient amount of data to provide meaningful and statistically reliable results. Additionally, the systems employed tend to be prohibitively expensive for use with most applications.

Contamination on a bonding surface is just one factor which can affect bond strength. Another parameter which can greatly affect the strength of a bond is the consistency of the thickness and the uniformity of chemical properties of the adhesive or other thin-film preparatory coatings applied to the bonding surface. And, of course, whether the adhesive completely covers the bonding surface also has an impact on the strength of the ultimate bond.

Generally, it is preferable to minimize the thickness of coatings applied to bonding surfaces. However, it is difficult to ascertain by non-contact methods the uniformity of a thin-layer coating or to readily ascertain whether the coating is applied to the entire surface.

The preparation of bonding surfaces is also important in obtaining an effective and consistent bond. Surface coatings or applications may be used to activate the surface to provide an enhanced chemical bond. When using such coatings or applications, the surface is prepared for bonding in a particular chemical state which must be consistent along the entire surface to maximize the strength of the bond. Of course, non-contact methods may not be employed to characterize the chemical state of a bonding surface.

For other applications it is also desirable to be able to characterize thin-layer coatings. For example, certain optical coatings, such as an anti-reflection coating, must have a consistent thickness to avoid adversely affecting the optics of the coated material. In the case of an anti-reflection coating, uniform thickness is prerequisite to causing the destructive interference of the reflected wave and thereby enabling the coating to effectively operate.

Thin films are also employed in some applications to obtain a particular color or appearance. In many cases, obtaining the desired aesthetic effect is dependent upon the consistency of the thickness and optical properties of the film.

From the foregoing it will be appreciated that it would be an advancement in the art to provide a system and process for the inspection of surfaces which would detect the presence of contamination, including low-level contamination which may not be detectible with prior-art visual inspection methods.

It would be a further advancement in the art to provide such a system and process which could be utilized in determining the identity of the contaminant.

It would be an additional advancement in the art to provide a surface inspection system and process which could measure the thickness of a thin film, thereby enabling determination of whether the level of contamination on a contaminated surface is within permissible limits.

Indeed, it would also be an advancement in the art if such a surface inspection system and process could work effectively to inspect and characterize thin films on a variety of surfaces and with different levels of roughness, including metal, phenolic and rubber surfaces.

It would be yet a further advancement in the art to provide such a system and process that could work efficiently and effectively in inspecting large surface areas and at a cost which would render the system suitable for use on a variety of applications.

It would be an additional advancement in the art if such a system and process for inspecting thin films could be utilized to characterize chemical and optical properties of thin films.

Such a surface inspection system and process is disclosed and claimed herein.

BRIEF SUMMARY AND OBJECTS OF THE INVENTION

The present invention is directed to a novel system for the non-destructive inspection of surfaces to detect and characterize the surface. The system includes a light source capable of generating a beam of infrared light. A lens focuses the incident beam at a discrete area on the surface to be inspected.

The system is configured such that a portion of the light reflected off the surface is directed by a lens into an optical filter arrangement. The optical filter arrangement separates the gathered portion of the reflected light into three sets of wavelengths. One of the sets of wavelengths corresponds to a target band from which information relating to the surface is sought and the two other sets of wavelengths include reference wavelengths located. Detectors are provided to measure the intensity of each of the sets of wavelengths.

A presently preferred embodiment of the invention is designed to detect and characterize hydrocarbon contaminants on a rough metal surface, such as a grit-blasted steel surface. For such a device, the target wavelength band corresponds to the absorption wavelength band for hydrocarbons which has its peak at about 3.4 microns.

For rough metal surfaces, including machined or grit-blasted metal surfaces, this preferred embodiment is configured to gather a portion of the back-scatter component of the reflected light. For smooth surfaces or rough non-metallic surfaces, it is presently preferred to adjust the system to gather a portion of the specular component of the reflected light.

In one embodiment of the present invention, the optical filter arrangement includes two optical filters positioned in line with each other. For characterizing hydrocarbons, the first filter is a high-pass filter with a cut-off value of about 3.3 microns. The second filter is a band-pass filter with a center wavelength of about 3.7 microns for light at an incident angle of 45 degrees. Thus, as the gathered portion of the reflected light passes through the first filter, all wavelengths less than about 3.3 microns are reflected towards a first reference detector. On the face of the first reference detector is positioned a band-pass filter with a center wavelength of about 3.2 microns. Thus, only light having a wavelength of from about 3.15 microns to about 3.25 microns is directed into the first reference detector.

Light from the gathered portion of the reflected light having a wavelength greater than about 3.3 microns are passed through the first filter and into the second filter. At the second filter, wavelengths from about 3.65 microns to about 3.75 microns are passed through to a second reference detector while the remaining wavelengths of light are reflected towards an absorption detector. On the face of the absorption detector is positioned a band-pass filter with a center wavelength of about 3.4 microns. Thus, only light having a wavelength of from about 3.35 microns to about 3.45 microns enters the absorption detector. So configured, only wavelengths of light corresponding to the absorption band of hydrocarbon—about 3.4 microns—are directed into the absorption detector.

The detectors generate an analog signal corresponding to the intensity of the wavelength of light they detect. The signal from each of the detectors is digitized with an analog-to-digital converter and analyzed by a signal processor.

A source detector is positioned to monitor the intensity of the incident beam, and, like the other detectors, generates a signal corresponding to the detected intensity. The signal from the source detector is passed through the analog-to-digital converter and monitored by the signal processor. The source detector is used to monitor fluctuations in the intensity of the incident beam of light. With this information, the signals produced by the other detectors are normalized to eliminate any error in the data resulting from those fluctuations.

The incident beam is preferably modulated with a chopper wheel or other means such that the effect of any ambient light is substantially eliminated. By modulating the incident beam, any ambient light introduced into the system would not be detected as a modulated signal. The system is designed to detect only the modulated component of the detected signal. Thus, the presence of ambient light does not effect the measurement of the system.

It is preferred to include a temperature sensor on each of the detectors. The sensitivity of the detectors varies as the temperature of the detectors changes. This sensitivity dependence is a known function of the temperature change. Thus, by monitoring the temperature of the detectors, compensation can be made to correct for the variance in the output of the detectors due to any drifts in detector temperature. In an effort to maintain the temperature of the detectors at a generally constant level, the detectors are thermoelectrically cooled.

In a preferred embodiment, a scanning apparatus is employed to rapidly change the point on the surface at which the beam of light is directed, thereby permitting the inspection of various locations on the surface. This may be accomplished by utilizing a scan table on which the sample is positioned and moving the scan table along an x-y axis by a scan controller. Alternatively, the scanning system may be moved relative to the surface being scanned to thereby scan a large surface area.

Advantageously, in a preferred embodiment, the light source, optical filter arrangement, detectors and electronics are all mounted on a common mounting board. Thus, a robotic arm may be attached to the mounting board to thereby position the scanning system relative to the surface to be inspected.

By synchronizing the signal processing and the scanning of the surface, data concerning contamination on the surface is generated. In one embodiment of the invention, successful scanning may be accomplished by directing the beam of light at discrete locations on the surface which are spaced about 0.25 centimeters apart and changing the point on the surface at which the beam of light is directed about every 0.02 seconds.

To obtain data concerning the thickness of a thin film as well as the existence of contamination, calibration plates may be used with the system. Such calibration plates may include one plate with no coating and one plate having a thin-film coating of known identity and thickness. By scanning calibration plates prior to inspecting a surface, the linear relationship between absorbance and thickness of the thin film may be determined. Because the thickness of the thin film is proportional to the absorption band size, once the linear relationship between absorbance and thickness is defined, the thickness of the thin film may readily be determined.

Thus, the present invention provides a system and process for the inspection of surfaces which detects the presence of contamination, including low-level contamination which may not be detectible with prior-art visual inspection methods. Additionally, the system and process of the present invention may be utilized in determining the identity of the contaminant.

The present invention also provides a surface inspection system and process which can be used to measure the thickness of a thin film, thereby enabling determination of whether contamination on a surface is within permissible limits.

Indeed, the present invention provides a surface inspection system and process which works effectively to inspect and characterize thin films on a variety of surfaces and with different levels of roughness, including metal, phenolic and rubber surfaces. The present invention works efficiently and effectively in inspecting large surface areas and at a cost which renders the system suitable for use on a variety of applications.

Additionally, the system and process of the present invention may also be used to characterize chemical and optical properties of thin films.

These and other objects and advantages of the present invention will become more fully apparent by examination of the following description of the preferred embodiments and the accompanying drawings.

BRIEF DESCRIPTION OF THE DRAWINGS

In order that the manner in which the above-recited and other advantages and objects of the invention are obtained, a more particular description of the invention briefly described above will be rendered by reference to the appended drawings. Understanding that these drawings only provide data concerning typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
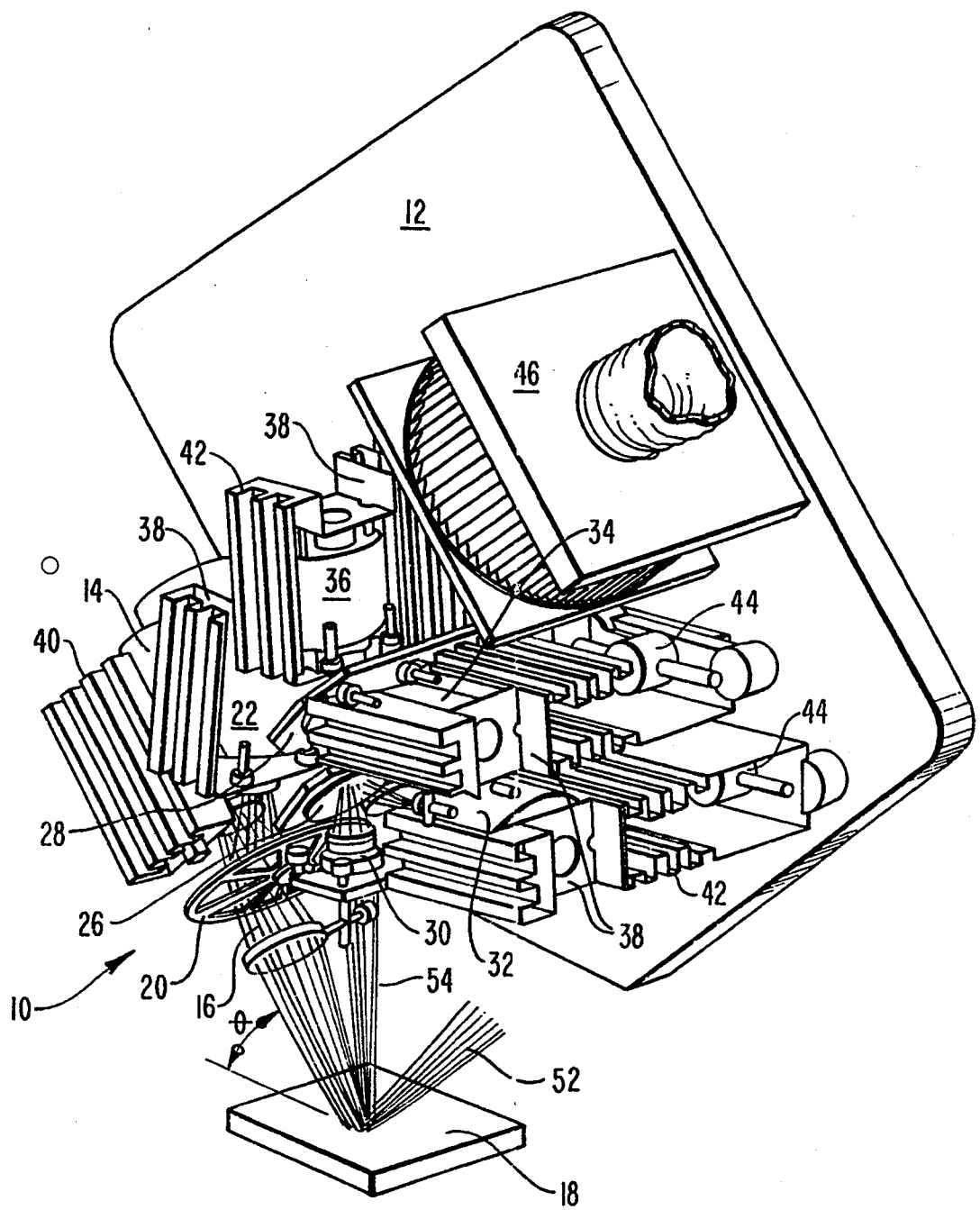
FIG. 1 is a perspective view of a presently preferred embodiment of the measurement head of the system of the present invention.

Reference is now made to the figures wherein like parts are referred to by like numerals throughout. With particular reference to FIG. 1, an optical scanning system according to the present invention is generally designated at 10. The system and process of the present invention may be used to inspect for and characterize virtually any thin film or surface for which absorption data or other optical properties are known or can be ascertained. Typical of the materials which are identified by the present invention are mold release agents such as silicone. The present invention may also be used to detect the presence of hydrocarbons on surfaces, such as oil condensed from oil vapors or HD2 grease used for rust protection. Additionally, the present invention may be utilized to measure thickness of thin films and to characterize certain chemical and optical properties.

The system 10 of FIG. 1 is a presently preferred embodiment designed for the detection and characterization of hydrocarbon contaminants on a rough metal surface. As explained below, modification of certain operating parameters of the system is necessary to achieve optimal utilization of the system as the type of surface varies and as the nature of the characterization sought is modified.

The system 10 includes a mounting plate 12 to which the various components of the system which comprise the measurement head are attached. A light source 14 generates an incident beam of light 16 which is directed towards a surface 18 to be inspected. The surface 18 illustrated in connection with this preferred embodiment of the invention is a grit-blasted metal surface.

Light source 14 is preferably a tungsten/halogen lamp of about 10 watt such as that made by Gilway Technical Lamp of Woburn, Mass. Such a light source 14 is optimized for near to mid infrared wavelengths. It is preferred that light sources having a small filament be utilized, thereby better simulating a point source of light.

When inspecting rough metal surfaces, such as grit-blasted steel surfaces, it is preferable to position the light source 14 such that the incident beam 16 is at an incident angle $\theta$ of approximately 45 degrees with respect to the surface 18 being inspected. If the system 10, of the present invention is being utilized to inspect smooth surfaces, such as smooth metal surfaces, polymer surfaces or polymer-coated metal surfaces, it has been found that results are optimized by orienting the incident beam 16 normal to the surface 18.

A chopper wheel 20 is positioned below the light source 14 and is configured with a series of blades which intercept the incident beam 16 as it is emitted from the light source 14. The chopper wheel 20 is further configured to rotate about a central axis at a predetermined rate such that the light being emitted from the light source 14 is modulated. A source detector 22 is positioned adjacent the light source 14 such that the incident beam 16 which is reflected off the chopper wheel 20 is directed into the source detector 22.

A preferred embodiment of the measurement head of the system 10 also includes an optical filter arrangement comprising a first optical filter 26 and a second optical filter 28. A lens 30 is positioned below the first optical filter 26 such that it may direct light reflecting off the surface 18 into the first optical filter 26.

An array of detectors is positioned about the optical filter arrangement. In this preferred embodiment, a first reference detector 32 is positioned to receive light reflected off the first optical filter 26. An absorption detector 34 is positioned to receive light reflected off the second optical filter 28. And, a second reference detector 36 is positioned to receive light passed through the second optical filter 28.

Each detector is preferably thermoelectrically cooled to enhance performance. A typical thermoelectric cooler is the TC7100 made by Vere, Inc. of New Kensington, Pa. Also, each detector provided with a heat sink 38 to dissipate the heat generated by thermoelectrically cooling the detector. The light source 14 is also provided with a heat sink 40. The heat sinks 38 and 40 are configured with cooling ribs 42 which improve the heat exchanging efficiency of the heat sinks. In the preferred embodiment, the heat sinks 38 and 40 are heat sinks such as those conventionally known for use in the art. While liquid nitrogen-cooled detectors may also be utilized, the thermoelectrically cooled detectors provide acceptable performance at a reasonable price.

The detectors and heat sinks are attached to the mounting plate 12 with bolts 44. A cooling fan 46 is attached at the upper portion of the mounting plate 12 to provide circulation of ambient air and thereby increase the effectiveness of the cooling ribs 42 on the heat sinks 38 and 40.

The operation of the system of the present invention is best explained with reference to FIG. 2. The optical scanning system 10 is initially positioned with respect to the surface 18 to be inspected. In this embodiment, the measurement head is preferably positioned such that the mounting plate 12 has an approximate 2.2 centimeter offset from the surface 18.

The light source 14 directs an incident beam 16 of infrared light through a source lens 50. Source lens 50 further directs the light towards the surface 18 and focuses the incident beam 16 at a discrete location on the surface 18. It is presently preferred that the lens 50 focus the incident beam 16 to an approximate 0.6 centimeter diameter beam on the surface 18.

The light reflecting off the surface includes a specular component 52 and a diffuse component. In this embodiment of the invention, the reflected light gathered for analysis 54 by the measurement head is taken from the back-scatter portion of the diffuse component of the reflected light. Indeed, it is preferable when inspecting rough metallic surfaces to gather a portion of the back-scatter component of the reflected light. As used herein, a surface is considered to be "rough" if its RMS (root mean square) roughness is approximately on the order of, or greater than, the magnitude of the wavelength of light being employed to evaluate the surface.

Importantly, in accordance with the teachings of the present invention, surface roughness actually enhances the ability of the system of the present invention to detect and quantitatively measure surface contamination. Generally, the sensitivity of the present invention in detecting and measuring contamination is proportional to the intensity of the electric field created by the incident beam at the surface. Hence, as surface roughness increases, there is greater tendency for multiple scattering which results in increased intensity in the electric field at the surface.

Because of this ability to successfully inspect rough surfaces, the present invention may be used to inspect surfaces of phenolic materials—materials which have proved particularly difficult to inspect by other methods. Carbon phenolics, for example, which have a randomly rough surface even when machined, can be efficiently and effectively inspected by practicing the teachings of the present invention.

If the surface is a smooth surface, it is presently preferred to gather and analyze a portion of the specular component 52 of the reflected light. Additionally, for rough non-metallic surfaces, it is also preferred to gather a portion of the specular component 52 of the reflected light.

Figure 2:
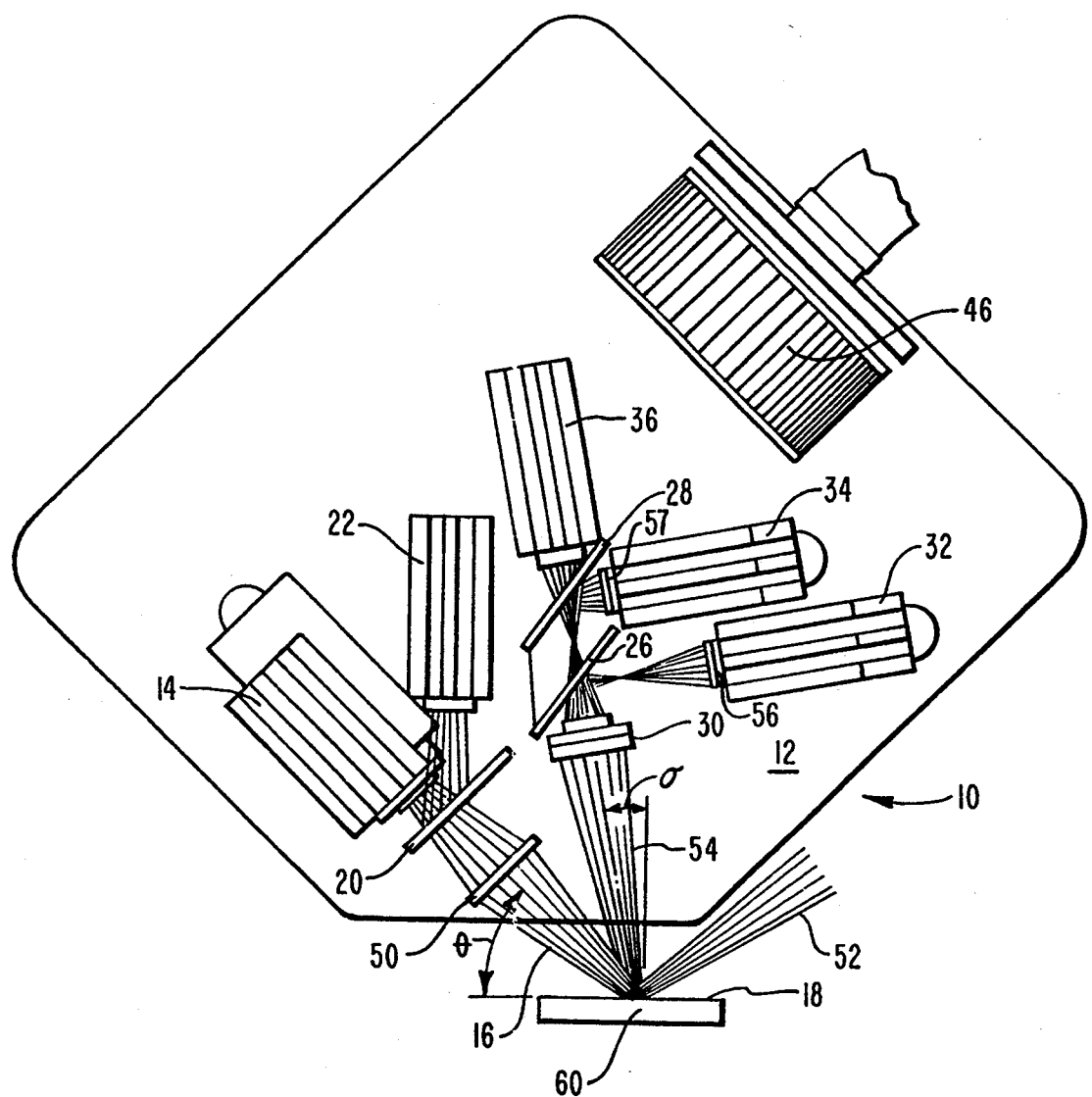
FIG. 2 is a schematic view of the measurement head of FIG. 1.

As viewed in FIG. 2, the lens 30 and the optical filter arrangement are configured with respect to the surface being inspected such that the portion of the reflected light 54 gathered for analysis by the system is at angle σ of about five to ten degrees with respect to the normal to the surface.

With continued reference to FIG. 2, the optical filter arrangement is positioned with filters 26 and 28 oriented at an approximate 45 degree angle with respect to the incoming beam 54. Lens 30 is configured such that it focuses the gathered light 54 at a point approximately midway between optical filters 26 and 28.

In this preferred embodiment used for inspecting and characterization hydrocarbon contaminants, filter 26 is a high-pass filter having a cut-off value of approximately 3.3 microns. Thus, all wavelengths of light in the gathered portion of the reflected light 54 which are less than about 3.3 microns are reflected by first optical filter 26 towards first reference detector 32.

On the face of first reference detector 32 is positioned a third optical filter 56. It is presently preferred that third optical filter 56 comprise a band-pass filter having a center wavelength of about 3.2 microns. Thus, only wavelengths of light from about 3.15 microns to about 3.25 microns are directed into first reference detector 32.

All wavelengths not reflected by the first optical filter 26 are passed through filter 26 and into second optical filter 28. In this embodiment, second optical filter 28 is a band-pass filter having a center wavelength of about 3.7 microns for light at an incident angle of 45 degrees. Thus, all wavelengths of light received by second optical filter 28 which are from about 3.65 microns to about 3.75 microns are passed through the filter, and all remaining wavelengths—from about 3.3 microns to about 3.65 microns and above about 3.75 microns—are reflected off the filter towards absorption detector 34.

On the face of absorption detector 34 is positioned a fourth optical filter 57. It is presently preferred that fourth optical filter 57 comprise a band-pass filter having a center wavelength of about 3.4 microns. Thus, only wavelengths of light from about 3.35 microns to about 3.45 microns are directed into absorption detector 34.

Detectors 32, 34 and 36 are each positioned to receive the three sets of wavelengths, as separated by the optical filters. Detectors 32, 34 and 36, as well as source detector 22, are all infrared detectors having capacity to detect the intensity of light in the near to mid infrared wavelengths. Thermoelectrically cooled detectors, such as the G21-3-66 detector sold by New England Photoconductor of Norton, Mass., have been found to be suitable in terms of performance and price.

The effect of passing the gathered light 54 through the series of filters 26, 28, 56 and 57 is to separate the light 54 into three sets of wavelengths. The light directed into the first reference detector 32 includes wavelengths of from about 3.15 microns to about 3.25 microns, the light directed into the absorption detector 34 includes wavelengths of from about 3.35 microns to about 3.45 microns, and the light directed into the second reference detector 36 includes wavelengths from about 3.65 microns to about 3.75 microns.

In the case of hydrocarbon inspection and characterization, the absorption band for hydrocarbons is between about 3.3 and about 3.6 microns, with its peak located at about 3.4 microns. Thus, the set of wavelengths which are directed into the absorption detector 34 correspond to the absorption band of hydrocarbons. By measuring the intensity of the light directed into the absorption detector, the presence of hydrocarbons on the inspection surface 18 can be ascertained.

The light detected by first and second reference detectors 32 and 36 thus corresponds to the wavelengths on each side of the absorption band. By detecting and measuring the intensity of light at reference wavelengths on each side of the absorption band, a more accurate measure of the absorbance of light at the absorption band may be obtained.

The absorbance is determined by initially determining the absorbance at the reference bands. The "base-line" absorbance is then determined by drawing a line between these two points on a graph plotting absorbance versus wavelength. The base-line absorbance at the peak absorption wavelength can then be identified as the point on the line at the peak wavelength of the absorption band. This base-line absorbance is then subtracted from the measured absorbance to obtain a more accurate reading of the actual magnitude of the hydrocarbon absorption band.

When scanning a smooth surface such as a polymer-coated metal surface, i.e., a surface whose RMS roughness is approximately the same order of magnitude as the wavelength of light being used, only one reference wavelength need be utilized. By definition, the amount of roughness is relatively uniform compared to the wavelength of light; thus, only one reference wavelength band is needed. In contrast, however, when the surface being inspected has varying roughness, two reference wavelength bands are preferred.

Of course, one of skill in the art will appreciate that a variety of types of optical filters may be employed to achieve the desired result of separating the target wavelength band from the reference band(s). Thus, although the present invention is described and illustrated as utilizing high-pass and band-pass filters, other types of optical filters, such as low-pass and notch filters, as well as combinations of different types of filters, may all be utilized in accordance with the teachings of the present invention.

In order to eliminate inaccuracies in the results which occur because of fluctuations in the intensity of the incident beam 16, the source detector 22 constantly monitors the intensity of the incident beam 16. Thus, while operating the system 10 of the present invention, the chopper wheel 20 rotates about its central axis to modulate the source beam 16.

The measurement head (FIG. 1) is preferably housed within a cover (not shown) to keep ambient light from affecting the measurements. Of course, any cover must include a windowed area to permit the incident beam 16 to contact the inspection surface 18 and to permit a portion of the reflected light 54 to be gathered and analyzed by the system 10. Thus, the possibility for some ambient light entering the system does exist.

The effects of any ambient light entering the system are substantially eliminated by modulating the incident beam with the chopper wheel. Any ambient light which does penetrate the system is not detected by any of the detectors as having a modulated amplitude. Because the system is designed to detect only the modulated component of the detected signal, the presence of ambient light does not effect the measurement of the system.

The source detector 22 receives the inverse modulation of light as that received by the surface 18. Thus, when the chopper wheel 20 is positioned to permit the source light to pass through the chopper wheel 20 and onto the surface 18, the source detector 22 detects no light. Further rotation of the chopper wheel 20 causes it to obstruct the incident beam 16, reflecting the beam into the source detector 22. The data gathered by the source detector 22 can be used to normalize the measurements taken by the detectors 32, 34 and 36 to reduce the effects in those measurements resulting from fluctuations in the intensity of the beam produced by light source 14.

It is preferred to include a temperature sensor in the system to monitor the temperature of each of the detectors. The sensitivity of the detectors varies as the temperature of the detectors changes. This sensitivity dependence is a known function of the temperature change. Thus, by monitoring the temperature of the detectors, compensation can be made to correct for the variance in the output of the detectors due to any drifts in detector temperature.

Figure 3:
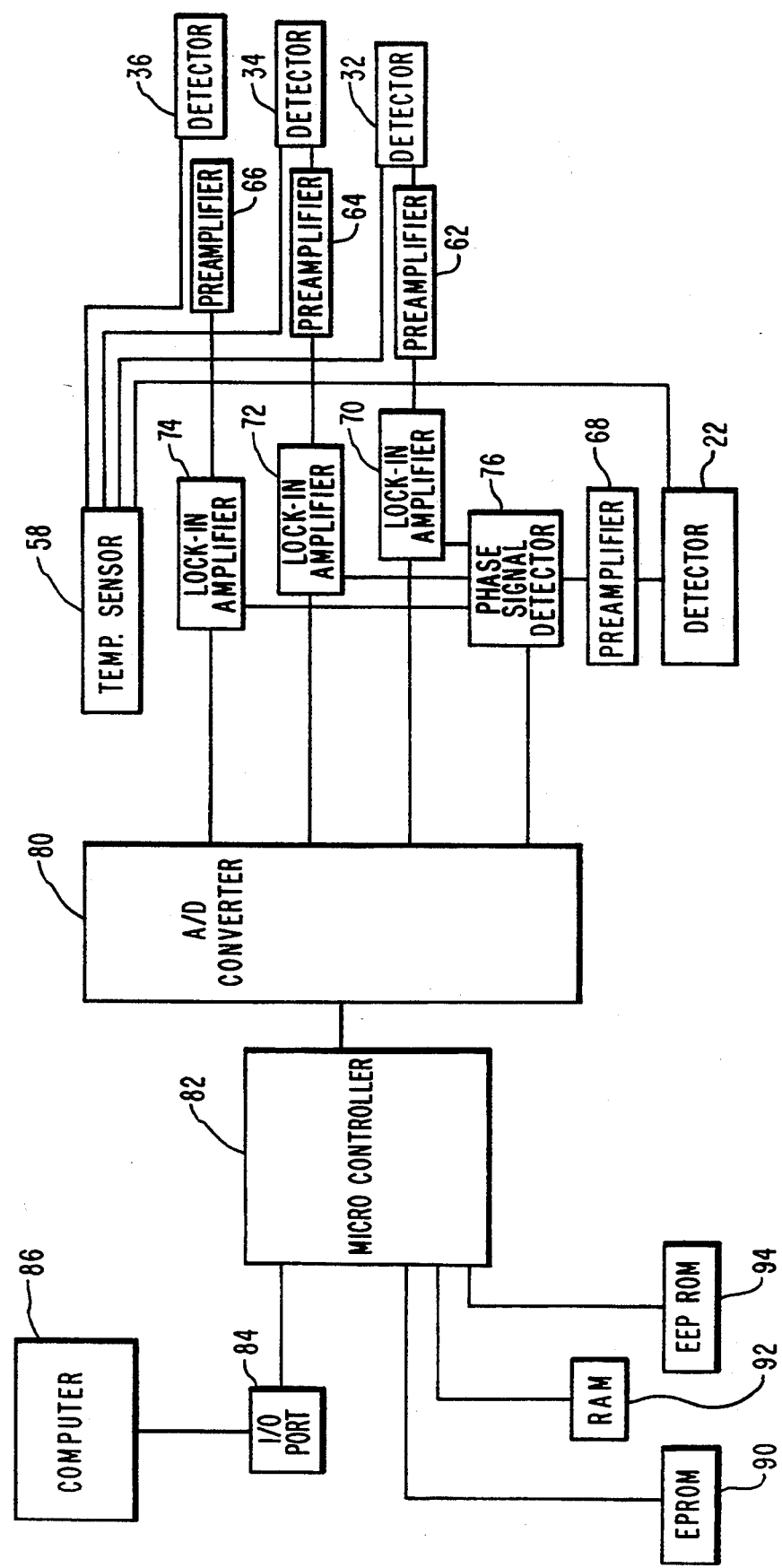
FIG. 3 is a schematic view of some of the electronic monitoring and feedback devices utilized in a presently preferred embodiment of the invention.

As illustrated in FIG. 3, a temperature sensor 58 is in communication with each of the detectors 22, 32, 34 and 36. This provides the ability to simultaneously monitor the temperature of all of the detectors and make compensation to account for temperature fluctuations.

In one embodiment of the present invention, the surface 18 being inspected is supported by a scan table 60. The scan table 60 is controlled by a scan controller. The scan table 60 and controller may be any of those controllers and tables which are commercially available, such as the 4000 Series controller and the HM-1212 table, both of which are sold by Design Components, Inc. of Franklin, Mass.

When utilizing a scan table 60, the measurement head is held in a stationary position while the surface 18 being scanned is moved by the scan table 60. While such an embodiment is presently preferred for a laboratory scale model of the invention wherein small surfaces are being scanned, it is not the preferred embodiment if the surface to be inspected is a large-area surface.

For use with large-area surfaces, it is preferred that mounting plate 12 be used in combination with a robotics system. This could be accomplished by attaching the mounting plate 12 to a robotic arm, for example. In such an embodiment, the surface to be scanned is held in a stationary position while the measurement head is moved relative to the surface 18 to obtain data from various discrete locations on the surface.

The analog signal generated by each detector 32, 34 and 36 is sent through preamplifiers 62, 64 and 66 corresponding to each detector. The preamplifiers 62, 64 and 66 amplify the signal to a useable level. A preamplifier 68 is also provided for the signal generated by the source detector 22.

The signals from detectors 32, 34 and 36 is then sent through lock-in amplifiers 70, 72 and 74. The lock-in amplifiers 70, 72 and 74 work in combination with a phase/signal detector 76. Because the light detected by the source detector 22 is reflected off the chopper wheel 20, the signal detected by the source detector 22 is approximately 180 degrees out of phase with the signal generated by the detectors 32, 34 and 36. Thus, the phase/signal detector 76 acts to full wave rectify the signal from the detectors 32, 34 and 36 and convert the AC signals from all the detectors to a DC signal having a level which is proportional to the amplitude of the original AC signals.

These DC signals are then digitized by an analog-to-digital converter 80 and read by a microcontroller 82. Microcontroller 82 is preferably an Intel 8032 microcontroller.

In addition to reading the signals from the detectors, microcontroller 82 is also linked via a serial input/output port 84 to a host computer 86. Thus, the microcontroller 82 recognizes commands from the host computer and does the appropriate gain stage selection to read the signals from the detectors.

In accordance with this preferred embodiment of the invention, the microcontroller 82 is used in combination with an erasable programmable read-only memory chip (EPROM) 90, a random access memory (RAM) 92 and an electronically erasable programmable read-only memory chip (EEPROM) 94. The EPROM 90 includes the operational software, or firm ware, for the microcontroller 82. The RAM 92 is used principally for temporary storage of transient data. The EEPROM 94 includes data for configuring the system 10.

The operational software within the EPROM 90 recognizes commands from the host computer. Additionally, the EPROM software provides signal acquisition from each of the three detectors 32, 34 and 36, the source detector 22 and the temperature sensor 58. In some embodiments of the invention, the EPROM 90 may be programmed to do all the calculations necessary to determine contamination level at the sample. Also, the EPROM 90 preferably reports error status in both hardware and software by providing error messages to the host computer 86.

In order to eliminate any noise or inconsistencies in the data due to physical size differences in the blades of the chopper wheel 22, the EPROM 90 also reads the A/D converter 80 over an integer number of electrical cycles of the chopper wheel 20. That number is then averaged to produce a mean value which can be used to correct the electrical signal produced by the detectors.

The EEPROM 94 includes the data which may be sent to the measurement head to properly configure the system for hardware variations. For example, the alignment of the measurement head may have to be adjusted depending on the surface to be scanned. Also, the EEPROM 94 stores the time over which the signals are integrated to eliminate error resulting from imperfectly sized chopper wheel blades. The data acquired from this integration process is saved in the EEPROM 94 thereby permitting the microcontroller 82 to have continual access to it to initialize itself as to the current operating conditions of the system.

As previously stated, the host computer 86 is electronically connected to microcontroller 82 through serial port 84. The host computer 86 is preferably an IBM compatible computer with at least an Intel 80386 processor, a 40 megabyte hard drive and eight megabytes of random access memory. A color monitor is preferably included which has EGA or higher resolution graphics capabilities. In a presently preferred embodiment, the host computer 86 operates in a Windows version 3.1 operating system. The host computer 86 further includes two serial ports which are preferably RS232 or RS422 ports.

The software of the host computer 86 controls some configuration parameters based on how the hardware is set up. Further, it controls the x-y motors on the scan table 60 which allow the sample to move with respect to the system. Additionally, the host computer 86 may include diagnostic software, though not necessary to run the system. The bulk of the software included on the host computer can be included in one of five categories: communications, configuration, scan, manual and "run head."

The communications software is also configured to permit the host computer 86 to send and receive messages to and from the microcontroller 82.

The configuration software is designed to hold all the parameters which are variable based on the specific hardware implementation. For example, if the detectors operate slightly differently, the configuration software will compensate for those differences.

The scan software defines what type of scan the measuring head will take and provides starting and ending coordinates for the scan. It also provides the step size for each position of the sample with respect to the measurement head. With the scan software, the scan parameters can be saved as files and subsequently retrieved for later use.

The scan software also permits the host computer 86 to perform inquiries from the measurement head and report back to the host computer to obtain the information from which absorbance values may be calculated and contamination level may be recorded. This data may be plotted on the monitor and/or stored as data files for later retrieval and analysis.

The "manual" component of the software provides the user of the system a means for individually viewing each of the detector signals. The manual software operates to divide the voltage by the gain level and multiplying by the responsivity of the detector to provide the detector power. The manual software also provides capability to display on screen the gain level and temperature of each detector while the system is operating. Additionally, it enables the scan table 60 to be moved to different positions. Thus, the manual software enables the temperature and change in absorbance to be visually monitored by the user of the system in near-real time.

Finally, the "run head" component of the software permits the voltage at the A/D converter 80 to be read for each detector as well as the voltage for the temperature sensor 58 at each detector. This portion of the software also permits the gain setting of the detectors to be adjusted to enable the impact of gain adjustment on the voltage to be viewed. When the host computer sends out measurement requests to the measurement head, the "run head" software will report any error conditions which are detected and display them on the screen.

The foregoing description of the software is merely exemplary of some of the parameters which might be controlled or monitored through the software. A complete listing of the message structure for the messages which are communicated between the host computer 86 and the microcontroller 82 in a presently preferred embodiment of the invention is attached hereto as Appendix A. Of course, one of skill in the art will readily be able to configure a set of instructions to operate the system in accordance with the specific parameters over which control or access is desired.

In the presently preferred embodiment of the invention, the electronics which control the system, with the exception of the host computer 86, are preferably mounted on the opposite side of mounting plate 12 (FIG. 1). Because a substantial amount of heat is generated by thermoelectrically cooling the detectors, as well as by the light source and chopper motor, during operation of the system, the mounting plate 12 acts as a thermal barrier to prevent the electronics from being exposed to increased temperatures.

In operation, the system 10 of FIGS. 1 and 2 is initially configured as explained herein depending on the particular thin film or contaminant for which inspection or characterization is thought and depending on the nature of the surface to be inspected. Once the system 10 has been set up for operation, the system is preferably calibrated prior to use. Because the relationship between the thickness of the contamination or thin film and the amount of absorbance of light at the absorption band is linear, the zero point and slope of that linear relationship must be determined by calibration in order to calculate the thickness of the contamination from the absorption data.

Calibration is performed by obtaining a calibration plate made of the same material and having the same roughness as the substrate to be inspected. In a preferred embodiment, five predetermined thicknesses of contamination are applied to approximately five different locations on the plate, thereby providing a sufficient number of data points that the linear relationship between absorption and thickness can readily be determined. The calibration plate should be representative of both the material type and the roughness level of the surface to be inspected.

The system 10 should be calibrated each time the substrate to be inspected is changed. Also, each time the filters are adjusted or the angle of incidence of the beam is altered, the system should be calibrated to regenerate the calibration curve.

Use of the optical scanning system 10 of the present invention permits the analysis of a variety of discrete locations of a surface to be conducted quickly, thereby enabling the system to be efficiently used in analyzing large surface areas. Once data has been obtained from one location of the surface, the system may be utilized to inspect an adjacent location of the surface and the process repeated until representative samples of the entire surface have been inspected. With data from representative samples of the entire surface, the computer 86 can generate an output indicating both the location of any contamination as well as its thickness.

It is presently contemplated that the system 10 be configured to permit surface scanning rates on the order of centimeters per second. A presently preferred embodiment has successfully scanned surfaces at a scan rate of about ten centimeters per second. However, one skilled in the art will appreciate that the surface scanning rate may be adjusted according to the requirements of the particular application. For example, tolerance for contaminants for some applications may be higher than for others, thereby permitting measurements to be taken farther apart and permitting faster scanning.

The present invention is capable of integrating over varying lengths of time. So configured, the system provides a mechanism to control the signal-to-noise ratio.

This data may be output in either graphical, numerical or machine-readable form. In graphical form, the data may be displayed as an image in which a different color or shade of gray is designated as corresponding to a predetermined thickness of the contamination. In a presently preferred embodiment of the invention, such a color scale image is preferred.

Alternatively, a surface image could be generated which appears as a three dimensional image on the screen. A surface image is advantageous for graphically illustrating relative thickness of the contamination as compared to the background noise level. A disadvantage to surface images is that some of the information is hidden by the peaks generated to form the image.

The computer 86 and microcontroller 82 are ideally programmed to synchronize the processing of the signal received from the detectors with the movement of the beam of light with respect to the surface being inspected. The synchronization of these two functions enables the computer to generate output correlating the data with the precise location on the surface to which it corresponds. One of ordinary skill in the art will appreciate that there are a variety of ways to program a computer to accomplish this objective.

Additionally, while the embodiment disclosed herein is designed for detecting a single contaminant, it will be appreciated that an optical filter arrangement could easily be configured to detect multiple absorption bands.

From the foregoing, it will be appreciated that the present invention provides a system and process for the inspection of surfaces which detects the presence of contamination, including low-level contamination which may not be detectible with prior-art visual inspection methods. Additionally, the system and process of the present invention may be utilized in determining the identity of the contaminant and to characterize chemical and optical properties of thin films.

The present invention also provides a surface inspection system and process which can be used to measure the thickness of a thin film, thereby enabling determination of whether contamination on a surface is within permissible limits. Also, the invention works effectively to inspect and characterize thin films on a variety of surfaces and with different levels of roughness, including metal, phenolic and rubber surfaces. The invention is especially suited for inspecting large surface areas at a cost which renders the system suitable for use on a variety of applications.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

1 Introduction

This document defines the message structure for messages passed between the Host Computer and the Surf-Map-IR Measurement Head. This message structure is defined as a serial protocol operating via an RS-422 (full duplex) bus.

The baud rate is set to 9600 baud. Each data byte will consist of one (1) start bit, 8 data bits, no parity, and one (1) stop bit.

Each message packet structure has the form of:
<ESC> <Type> <Message (Type Dependent)> <CR>
(each element of the message is shown enclosed by brackets).

All data embedded in messages is represented by ASCII characters (no binary data is allowed).

The messages will follow a "master-slave" protocol to ensure that only one computer is transmitting on the RS-422 bus at a time. The host computer (master) must initiate all messages and the measurement head (slave) must respond to each message with either a positive or negative acknowledgement. Each response message will be defined at the time the message from the master is defined.

A normal positive acknowledgement message is:
<ESC> <*> <CR>
A normal negative acknowledgement message is:
<ESC> <?> <HH> <CR>
where <HH> is an error code (coded in hexadecimal) transmitted from the measurement head to the host. These error codes are:

ERR_NONE 00
No error occurred.
ERR_ADC_MIN_MAX_VAL 01
Error in the analog to digital converter maximum or minimum value configuration message.
ERR_INTEG_TIME 02
Error in the integration time configuration message.
ERR_TIME_CONSTANT 03
Error in the time constant time configuration message.
ERR_DET_WAVE_MAP 04
Error in the configuration message that maps detector index to wavelength index.
ERR_WAVE_VAL_INDEX_MAP 05
Error in the configuration message that sets the wavelength values.
ERR_GAIN_VAL 06
Error in the configuration message that sets the gain values.
ERR_INTEG_TIME_RES 07
Error in the configuration message that sets the integration time resolution.
ERR_SIGNAL_PHASE 08
Error in the configuration message that sets the signal phase.
ERR_DET_RESPONSIVITY 09
Error in the configuration message that sets the detector's responsivity.
ERR_DELTA_DET_RESP 0A
Error in the configuration message that sets the detector's delta responsivity.
ERR_THERM_TEMP_COEFF 0B
Error in the configuration message that sets the thermistor temperature coefficients.
ERR_NOM_REF_VOLTAGE 0C
Error in the configuration message that sets the nominal reference voltage.
ERR_NOM_REF_POWER 0D
Error in the configuration message that sets the nominal reference power.
ERR_REF_GAIN_LEVEL 0E
Error in the configuration message that sets the nominal reference gain level.
ERR_DAUGHTER_NOT_FOUND 0F
Error in the configuration message that tells the head to install a daughter board, due to the fact that the head cannot recognize an installed daughter board.
ERR_CUR_REF_SAMPLE 10
Error in the configuration message that sets the current reference sample data.
ERR_TEMP_DET_MAP 11

Error in the configuration message that maps the thermistors to detectors.

ERR_TE_MEAS_OFF_VOLT 12
Error in setting the thermistor measurement offset voltage.

ERR_TE_CNTL_CUR 13
Error in setting the thermistor current source current value.

ERR_THERM_RESISTANCE 14
Error in setting the thermistor excitation voltage divider resistance value.

ERR_RESP_TEMP_CORRECT 15
Error in the configuration message that indicates to the head to turn on/off responsivity correction as a function of temperature.

ERR_MEAS_MODE 16
Error in configuring the measurement mode as FAST or SLOW.

ERR_SIG_ACQ_TIMEOUT 17
Error in setting the signal acquisition timeout time.

ERR_DELTA_A_TO_CONTAM 18
Error in setting the conversion factor for translating delta absorbance into a contamination value.

ERR_TEMP_DIFF_AMP_GAIN 19
Error in setting the temperature control differential amplifier gain value.

ERR_WRITE_CONFIG 1A
Error in writing the configuration data to EEPROM.

ERR_BAD_PARAM 80
A bad parameter was present in a message.

ERR_FLOAT_CONVERSION 81
A problem was encountered in converting a floating point value.

ERR_INTEGER_CONVERSION 82
A problem was encountered in converting an integer value.

ERR_HEX_STR_CONVERSION 83
A problem was encountered in converting a hexadecimal value.

ERR_NOT_IMPLEMENTED_FE
The message type is not implemented in the measurement head ERR_UNRECOGNIZED CMND FF
The command (message) is not recognized by the measurement head The message structures can be broken into several major categories. These categories are defined below under major headings. Each message type is defined under one of these major categories.

2 Power Failure

The measurement head will set the most significant bit of it's message type if a power failure has occurred. This bit will indicate to the host that any parameters that have been sent to the head that have not been written to the head's non-volatile memory have been lost. The head will continue setting this bit with every message response until a P type message is sent from the host to the head. The for mat of the P type message is:
<ESC> <P> <CR>

3 Configuration

Each configuration message has a message type of 'C' followed by a sub type. The subtype defines what the rest of the message structure contains.

The general format of the configuration message is:
<ESC> <C> <2 Decimal Digit Subtype> <Message (Subtype Dependent)> <CR>

The configuration messages will update the head's current operating parameters. To make the changes permanent, a 'Write Configuration' (<C> <99>) message must be sent to the head, so the head will power up with the desired parameters as the current operating parameters.

3.1 Configuration Subtypes

3.1.1 01-Maximum/Minimum ADC Readings
Message Content:
<ESC> <C> <01> <HHHH> <HHHH> <CR>

Two 4 Digit Hex Numbers representing ADC voltage in millivolts. Max value is 4500, Min value is −4500. This value is offset by 4500 so min will be 0, max will be 9000 (2328 Hex), If this message is sent with no parameters (i.e. <ESC>C01 <CR>) the measurement head will report back it's current settings with a C01 type message.

A positive acknowledgement (the message was OK) will require the head to respond with a normal positive acknowledgement message. A negative acknowledgement (something wrong with the message) will require the head to respond with a normal negative acknowledgement message.

Default values:
8800 and 4700 decimal (4.3 volts and 0.2 volts).

3.1.2 02-Integration Time
Message Content:
<ESC> <C> <02> <1> <G> <HHHHHH> <CR>

This message sets the integration time for each detector as integration time per gain level per detector index. Integration time is in hundredths of milliseconds and is represented by a 6 digit hex number.

The <I> in the message is a one digit hex number which is the detector index. The <G> in the message is a one digit hex number which is the gain level index. The detector index, gain level and integration time can be repeated for each detector index and each gain level in the message (if desired).

A <C> <02> message with, only <I> and <G> contained in the message (no integration time specified) will cause the measurement head to respond with it's current integration time settings for the given detector and gain level.

A positive acknowledgement (the message was OK) will require the head to respond with a normal positive acknowledgement message. A negative acknowledgement (something wrong with the message) will require the head to respond with a normal negative acknowledgement message.

Default values:
33.33 msec (3333).

3.1.3 03-Time Constant Time
Message Content:
<ESC> <C> <03> <HHHHHH> <CR>

This message sets the time constant time in the measurement head. Time is in hundredths of milliseconds and is represented by a 6 digit hex number.

A <C> <03> message with no parameters will cause the measurement head to respond with it's current time constant time in a <C> <03> message format.

A positive acknowledgement (the message was OK) will require the head to respond with a normal positive acknowledgement message. A negative acknowledgement will require the head to respond with a normal negative acknowledgement message.
Default value:
3.3 msec (0330).

3.1.4 04-Map Detector Index To Wavelength Index

Message Content:

`<ESC> <C> <04> <D> <W> <CR>`

This message maps the detector index (0-2; reference detector is fixed) to the specified wavelength. All 3 detector indices may be mapped with a single message if desired by repeating the `<D>` and `<W>` parameters in the message.

A `<C> <04>` message with no parameters will cause the measurement head to respond with it's current detector to wavelength map settings.

A positive acknowledgement (the message was OK) will require the head to respond with a normal positive acknowledgement message. A negative acknowledgement (something wrong with the message) will require the head to respond with a normal negative acknowledgement message.

An invalid (negative) acknowledgement message may be generated if a detector is mapped to more than one wavelength or if a wavelength is mapped to more than one detector (Note that the wavelength mapping will still be performed. It is up to the host computer to note that a negative acknowledgement has occurred. The recommended procedure is to remap all detectors to wavelength indices in the same messages).

Defaults:
Detector 0→Wavelength 0
Detector 1→Wavelength 1
Detector 2→Wavelength 2

3.1.5 05-Assign Wavelength Value To Wavelength Index

Message Content:

`<ESC> <C> <05> <W> <HHHH>, <CR>`

This message is used to assign a wavelength value to a wavelength index. The `<W>` in the message is the wavelength index (0-2). The wavelength is in nanometers and is a 4 digit hex value. Note that wavelengths may be assigned to all wavelength indices within one message by repeating the wavelength indices and values for each wavelength index.

A message sent with no parameters will cause the measurement head to respond with its current wavelength values for each wavelength index.

The wavelength for wavelength index 0 must be the highest wavelength value and the wavelength for wavelength index 2 must be the lowest wavelength value. A negative acknowledgement will be generated by the head if these conditions are not met, however the wavelength values will still be assigned. It is recommended that wavelength values for all wavelength indices be assigned with one message.

A positive acknowledgement (the message was OK) will require the head to respond with a normal positive acknowledgement message. A negative acknowledgement (something wrong with the message) will require the head to respond with a normal negative acknowledgement message.

Defaults:
Wavelength index 0→3700 nanometers
Wavelength index 1→3390 nanometers
Wavelength index 2→3200 nanometers

3.1.6 06-Assign Gain Value

Message Content:

`<ESC> <C> <06> <D> <G> <±> <M.MM> <E> <±> <ee> <CR>`

This message is used to assign an electronic gain value to a gain level for a particular detector index. The `<D>` in the message is the detector index (0-3) and the `<G>` in the message is the gain index (0-3). The gain is a floating point number which is represented by:

$\pm M.MM \pm ee$

Where M.MM is the mantissa which contains 3 digits of significance and ee is the exponent which may range from −99 to +99.

Note that gain levels for more than one detector and/or wavelength index may be sent in the same message by repeating the detector index `<D>`, the gain index `<G>` and the floating point value for each detector index and each gain index that is to be set.

Note also that detector index 3 is used to set and retrieve the gain levels for the reference detector.

A `<C> <06>` message followed by the detector index and gain index with no gain value allows the head to respond with the current gain settings for the detector index and gain index.

A positive acknowledgement (the message was OK) will require the head to respond with a normal positive acknowledgement message. A negative acknowledgement (something wrong with the message) will require the head to respond with a normal negative acknowledgement message.

Defaults for each Detector index:
Gain index 0→+1.35E+07
Gain index 1→+1.35E+08
Gain index 2→+1.35E+09
Gain index 3→+1.35E+10

3.1.7 07-Integration Time resolution

Message Content:

`<ESC> <C> <07> <HHHHHH> <CR>`

This message is used to set the integration time resolution (ie. how much time elapses per revolution of the chopper wheel. This time is represented in hundredths of milliseconds. A `<C> <07>` message with no additional parameters allows the head to respond with the current integration time resolution.

A positive acknowledgement (the message was OK) will require the head to respond with a normal positive acknowledgement message. A negative acknowledgement (something wrong with the message) will require the head to respond with a normal negative acknowledgement message.

Default:
16.67 milliseconds (1667).

3.1.8 08-Set Signal Phase

Message Content:

`<ESC> <C> <08> <P> <CR>`

This message is used to set the phase of the signal with respect to the reference. If `<P>` is a zero, the signal is in phase with the reference, if `<P>` is a one, the signal is 180° out of phase with 'the reference. A `<C> <08>` message with no phase parameter allows the head to respond with the current signal phase setting.

A positive acknowledgement (the message was OK) will require the head to respond with a normal positive acknowledgement message. A negative acknowledgement (something wrong with the message) will require the head to respond with a normal negative acknowledgement message.

Default:

0-The signal is in phase with the reference.

3.1.9 09-Nominal Detector Responsivity (A/W)
Message Content:

<ESC> <C> <09> <D> <±> <M.MM> <E> <±> <ee> <CR>

This message is used to set the nominal detector responsivity when the detector is cooled at −40° C. This responsivity is also used if detector responsivity correction for temperature is turned off. The responsivity is set per detector index <D>. More than one detector's responsivity may be set by repeating the detector index <D> and the responsivity value. A <C> <09> message with no parameters causes the measurement head to report the current responsivity setting for each detector index.

The responsivity is a floating point number which is represented by:

±M.MM±ee

Where M.MM is the mantissa which contains 3 digits of significance and ee is the exponent which may range from −99 to +99.

A positive acknowledgement (the message was OK) will require the head to respond with a normal positive acknowledgement message. A negative acknowledgement (something wrong with the message) will require the head to respond with a normal negative acknowledgement message.

Defaults for each detector index:
+4.00E−03 (A/W).

3.1.10 10-Delta Detector Responsivity (A/W)
Message Content:

<ESC> <C> <10> <D> <±> <M.MM> <E> <±> <ee> <CR>

This message is used to set the change in detector responsivity as a change in temperature in degrees centigrade from −40° C. The change in temperature is positive as measured from −40° C. The number may be positive or negative. The delta responsivity is set per detector index <D>. More than one detector's delta responsivity may be set by repeating the detector index <D> and then the delta responsivity value. A <C> <10> message with no parameters causes the measurement head to report the current delta responsivity setting for each detector index.

The delta responsivity is a floating point number which is represented by:

±M.MM±ee

Where M.MM is the mantissa which contains 3 digits of significance and ee is the exponent which may range from −99 to +99.

A positive acknowledgement (the message was OK) will require the head to respond with a normal positive acknowledgement message. A negative acknowledgement (something wrong with the message) will require the head to respond with a normal negative acknowledgement message.

Defaults for each detector index:
+0.00E+00 (A/W/°C.).

3.1.11 11-Thermistor Temperature Coefficients
Message Content:

<ESC> <C> <11> <T> <±> <M.MM> <E> <±> <ee> <±> <M.MM> <E> <±> <ee> <±> <M.MM> <E> <±> <ee> <CR>

This message is used to set the temperature calculation coefficients for the detector thermistors by thermistor index. The temperature is calculated by the following equation:

$$1/T = A + B(\ln R_T) + C(\ln R_T)^3$$

Where A, B, and C are the temperature coefficients set by this message, $R_T$ is thermistor resistance in kOhms, and T is degrees Kelvin.

Each coefficient (A,B,C) is a floating point number which is represented by:

±M.MM±ee

Where M.MM is the mantissa which contains 3 digits of significance and ee is the exponent which may range from −99 to +99.

Note that the message to set coefficients is preceded by the thermistor index <T> and then the message must include three floating point numbers which are the coefficients A,B and C. Setting temperature coefficients for more thermistor indices may be accomplished in the same message by repeating the thermistor index <T> and then the three temperature coefficients. A <C> <11> message with only the thermistor index <T> will cause the measurement head to report back the temperature coefficients for that particular thermistor index.

A positive acknowledgement (the message was OK) will require the head to respond with a normal positive acknowledgement message. A negative acknowledgement (something wrong with the message) will require the head to respond with a normal negative acknowledgement message.

Defaults for each thermistor index:
A=3.33E−03.
B=3.11E−04
C=2.45E−06

3.1.12 12-Nominal Reference Voltage (millivolts)
Message Content:

<ESC> <C> <12> <HHHH> <CR>

This message is used to set the nominal voltage returned by the ADC when the reference voltage is read at the nominal reference gain level. This value is used to normalize the receiver signal for any fluctuations in source signal. The message consists of a 4 digit hex number which represents the reference voltage in millivolts and can range from 0 to 4500 decimal.

A <C> <12> message with no parameters causes the measurement head to report back the current reference voltage value with a <C> <12> message response.

A positive acknowledgement (the message was OK) will require the head to respond with a normal positive acknowledgement message. A negative acknowledgement (something wrong with the message) will require the head to respond with a normal negative acknowledgement message.

Default:
2250 Decimal=2.25 Volts

3.1.13 13-Nominal Reference Power
Message Content:

<ESC> <C> <13> <±> <M.MM> <E> <±> <ee> <CR>

This message is used to set 'the nominal reference power that is associated with the nominal reference voltage. This number is used more or less to quantify the amount of power produced by the source. The number is represented in watts.

The nominal reference power is a floating point number which is represented by:

±M.MM±ee

Where M.MM is the mantissa which contains 3 digits of significance and ee is the exponent which may range from −99 to +99.

A <C> <13> message with no parameters causes the measurement head to report back the current nominal reference power with a <C> <13> message response.

A positive acknowledgement (the message was OK) will require the head to respond with a normal positive acknowledgement message. A negative acknowledgement (something wrong with the message) will require the head to respond with a normal negative acknowledgement message.

Default:
+1.00E-04=0.1 milliwatt

3.1.14 14-Reference Gain Level
Message Content:
<ESC> <C> <14> <G> <CR>

This message is used to set the gain level of the reference detector. The same gain level is used at all times and for all readings. The <G> in the message is the gain level index (0–3).

A <C> <14> message with no parameters causes the measurement head to report back the current reference gain level index with a <C> <14> message response.

A positive acknowledgement (the message was OK) will require the head to respond with a normal positive acknowledgement message. A negative acknowledgement (something wrong with the message) will require the head to respond with a normal negative acknowledgement message.

Default:
0=Gain level (index) 0

3.1.15 15-Install/Uninstall Daughter Board
Message Content:
<ESC> <C> <15> <1> <CR>

This message is used to inform the measurement head if it's daughter board is installed. The <I> parameter embedded in the message is set to 0 if the daughter board is not installed and 1 if the daughter board is installed, A <C> <15> message with no parameters caused the measurement head to report back the current daughter board installation status with a <C> <15> message response.

If a daughter board is not installed, separate integration times for each detector are used. If the board is installed, the longest integration time associated with a detector is used while reading all 4 detectors. If the daughter board is not installed, the gain levels for detector 0 are used as the signal gain values.

A positive acknowledgement (the message was OK) will require the head to respond with a normal positive acknowledgement message. A negative acknowledgement (something wrong with the message) will require the head to respond with a normal negative acknowledgement message.

Default:
0=Daughter board is not installed

3.1.16 16-Current Reference Sample Data
Message content:
21 ESC> <C> <16> <±> <M.MM> <E> <±> <EE> <±> <M.MM> <E><±> <ee> <±> <M.MM> <E> <±> <ee> <CR>

This message is used to get the powers measured from the reference sample to provide the baseline measurements, Each power is represented by a floating point number
±M.MM±ee where M.MM is the mantissa which contains 3 digits of significance and ee is the exponent which may range from −97 to +99.

The powers in the message are arranged in order of wavelength where the first number is the highest wavelength (3.7 microns) and the third number is the lowest wavelength (3.2 microns).

A <C> <16> message with no parameters causes the measurement head to report back the current reference sample powers with a <C> <16> response.

A positive acknowledgment (the message was OK) will require the head to respond with a normal positive acknowledgment message.

A negative acknowledgment (something wrong with the message) will require the head to respond with a negative acknowledgment message.

3.1.1 7 17-Map Temperature Index to Detector Index
Message Content:
<ESC> <C> <17> <T> <D> <CR>

This message maps the temperature index (0–3; reference detector is index 3) to the specified detector index. All 4 temperature indices may be mapped with a single message if desired by repeating the <D> and <W> parameters in the message.

A <C> <17> message with no parameters will cause the measurement head to respond with it's current temperature to detector map settings.

A positive acknowledgement (the message was OK) will require the head to respond with a normal positive acknowledgement message. A negative acknowledgement (something wrong with the message) will require the head to respond with a normal negative acknowledgement message.

An invalid (negative) acknowledgement message may be generated if a temperature index is mapped to more than one detector index or if a detector index is mapped to more than one temperature index (Note that the temperature mapping will still be performed. It is up to the host computer to note that a negative acknowledgement has occurred. The recommended procedure is to remap all temperature indices to detector indices in the same messages.

Defaults:
Temperature 0→Detector 0 (Temperature 0 is the feedback controlled temperature)
Temperature 1→Detector 1
Temperature 2→Detector 2
Temperature 3→Reference Detector

3.1.18 18-Set T.E. Measurement Offset Voltage
Message Content:
<ESC> <C> <18> <HHHH> <CR>

One 4 Digit Hex Number representing the temperature offset voltage in millivolts. Max value is 4500, Min value is −4500. This value is offset by 4500 so min will be 0, max will be 9000 (2328 Hex).

If this message is sent with no parameters (i.e. <ESC> <C> <18> <CR>) the measurement head will report back it's current settings with a C18 type message.

A positive acknowledgement (the message was OK) will require the head to respond with a normal positive acknowledgement message. A negative acknowledgement (something wrong with the message) will require the head to respond with a normal negative acknowledgement message.

Default value:

5700 (1.2 volts).

3.1.19 19-Set T.E. Controller Current Source Current Value (in μAmps)

Message Content:

<ESC> <C> <19> <HHHHHH> <CR>

One 6 Digit Hex Number representing the current source current in microamps.

If this message is sent with no parameters (i.e. <ESC> <C> <19> <CR>) the measurement head will report back it's current settings with a C19 type message.

A positive acknowledgement (the message was OK) will require the head to respond with a normal positive acknowledgement message. A negative acknowledgement (something wrong with the message) will require the head to respond with a normal negative acknowledgement message.

Default value:

100 (100 μamps).

3.1.20 20-Set Thermistor Excitation Voltage Divider Resistance Value (Ohms)

Message Content:

<ESC> <C> <20> <HHHHHH> <CR>

One 6 Digit Hex Number representing the excitation voltage divider resistance value in Ohms If this message is sent with no parameters (i.e. <ESC> <C> <20> <CR>) the measurement head will report back it's current settings with a C20 type message.

A positive acknowledgement (the message was OK) will require the head to respond with a normal positive acknowledgement message. A negative acknowledgement (something wrong with the message) will require the head to respond with a normal negative acknowledgement message.

Default value:

28000 (6D60H or 28 kOhms).

3.1.21 21-Turn ON/OFF Responsivity Temperature Correction

Message Content:

<ESC> <C> <21> <T> <CR>

This message is used to turn off or on detector responsivity correction as a function of temperature. <T> is 0 to turn off responsivity correction, 1 to turn on responsivity correction.

If this message is sent with no parameters (i.e. <ESC> <C> <21> <CR>) the measurement head will report back it's current responsivity ON/OFF setting with a C21 type message.

A positive acknowledgement (the message was OK) will require the head to respond with a normal positive acknowledgement message. A negative acknowledgement (something wrong with the message) will require the head to respond with a normal negative acknowledgement message.

Default value:

0-Detector responsivity correction is OFF.

3.1.22 22-Set Measurement Mode (Fast/Slow)

Message Content:

<ESC> <C> <22> <M> <CR>

This message is used to set the instrument's measurement speed. Slow mode requires the instrument to wait 5 time constants after a gain change, fast mode only requires the instrument to wait 2 time constants. <M> is 0 to run in fast mode, 1 to run in slow mode.

If this message is sent with no parameters (i.e. <ESC> <C> <22> <CR>) the measurement head will report back it's current measurement mode setting with a C22 type message.

A positive acknowledgement (the message was OK) will require the head to respond with a normal positive acknowledgement message. A negative acknowledgement (something wrong with the message) will require the head to respond with a normal negative acknowledgement message.

Default value:

0-Measurement Mode is FAST.

3.1.23 23-Set Signal Acquisition Timeout Time

Message Content:

<ESC> <C> <23> <HHHHHH> <CR>

This message is used to set the signal acquisition time of the instrument. If the instrument is 'hunting' for the gain level to make the measurement, exceeding this time instructs the instrument to give up and abort the signal acquisition. The signal acquisition time is set by a 6 digit hex number representing the signal acquisition time in milliseconds.

If this message is sent with no parameters (i.e. <ESC> <C> <23> <CR>) the measurement head will report back it's current measurement mode setting with a C23 type message.

A positive acknowledgement (the message was OK) will require the head to respond with a normal positive acknowledgement message. A negative acknowledgement (something wrong with the message) will require the head to respond with a normal negative acknowledgement message.

Default value:

1000-Signal acquisition timeout is 1 second.

3.1.24 24-Set Conversion Factor for translating Delta Absorbance

Message content:

<ESC> <C> <24> <±> <ee> <CR>

This message sets the conversion factor for linearly translating Delta Absorbance to contamination level.

Conversion factor is:

±M.MM±ee

Where M.MM is the mantissa containing 3 digits of significance and ee is the exponent which may range from −99 to +99.

A <C> <24> message with no parameters causes the measurement head to report back the current conversion factor with a <C> <24> response.

A positive acknowledgement (the message was OK) will require the head to respond with a normal positive acknowledgement message.

A negative acknowledgment (something wrong with the message) will require the head to respond with a negative acknowledgment message.

3.1.25 25-Set Temperature Differential Amplifier Gain

Message Content:

<ESC> <C> <25> <HHHHHH> <CR>

This message is used to set the gain level of the electronics used to amplify the signal received from the thermistors for detector temperature calculations. The gain value is set by a 6 digit hex number representing the gain value in millivolts/volt, If this message is sent with no parameters (i.e. <ESC> <C> <25> <CR>) the measurement head will report back it's current measurement mode setting with a C25 type message.

A positive acknowledgement (the message was OK) will require the head to respond with a normal positive acknowledgement message. A negative acknowledgement (something wrong with the message) will require the head to respond with a normal negative acknowledgement message.

Default value:
7900 (decimal) millivolts/volt

3.1.26 26-Turn ON/OFF T.E. Controller

Message Content:
<ESC> <C> <26> <T> <CR>

This message is used to turn on or off the Thermo-Electric (T.E) cooler controller that is used to cool the signal detectors. The state of the T.E. controller is set by <T>. <T> is 1 to turn on the T.E. controller, 0 to turn off the T.E. controller. The measurement head will power up with either the T.E. controller on or off, based on the state of the controller when the configuration data is saved to EEPROM.

3.1.27 97-Fall Back to Last Configuration

Message Content:
<ESC> <C> <97> <CR>

This message instructs the measurement head to re-read the last configuration data that was saved to EEPROM and to use this data as current measurement parameters.

3.1.28 98-Erase Configuration (Rely on Default Data)

Message Content:
<ESC> <C> <98> <CR>

This message causes the measurement head to rely on the default configuration that was originally programmed into the firmware. This message is useful to allow the measurement head to fall back to pre-configured values.

3.1.29 99-Write Configuration

Message Content:
<ESC> <C> <99> <CR>

This message causes the measurement head to write the measurement parameters that the head is currently operating with to EEPROM. The head will read the EEPROM on power-up and utilizes these measurement parameters as the current measurement parameters (unless changed with another configuration message).

4 Measurement Settings

Each measurement setting message has a message type of 'S' followed by a sub type. The subtype defines what the rest of the message structure contains.

The general format of the configuration message is:
<ESC> <S> <2 Decimal Digit Subtype> <Message (Subtype Dependent)> <CR>

The measurement setting messages will update the head's current operating parameters but will not be configuration parameters that may be saved to non-volatile memory.

4.1 Measurement Setting Subtypes

4.1.1 01-Set Detector Current Gain Level

Message Content:
<ESC> <S> <01> <D> <G> <CR>

This message is used to force, the gain level of a detector specified by detector index <D> to the gain level index specified by <G>. <D> and <G> may be repeated in the message for each valid detector index present in the measurement head.

5 Measurements

Each configuration message has a message type of 'M' followed by a sub type. The subtype defines what the rest of the message structure contains.

The general format of the configuration message is:
<ESC> <M> <2 Decimal Digit Subtype> <Message (Subtype Dependent)> <CR>

The measurement setting messages will cause the head to measure and report back with the desired value(s). Most messages require a head response message back. Some messages will cause the head to respond with a "wait" message in which case the host must re-enquire the head until the head responds with a "complete" message. Typically, while the head is in "wait" mode, the host can send an "abort" message to cause the head to abort the current acquisition. These protocols are detailed under the appropriate section where applicable.

5.1 Measurement Subtypes

5.1.1 01-Measure Detector(s) Voltage at Current Gain Level

Host Message Content:
<ESC> <M> <01> <D> <CR>

Where <D> is:
1-Detector 0
2-Detector 1
3-Detector 0 & 1
4-Detector 2
5-Detector 0 & 2
6-Detector 1 & 2
7-Detector 0, 1, & 2

The measurement head responds with an <M> <01> message after the signal acquisition is complete.

Measurement Head Message Content:
<ESC> <M> <01> <D> <HHHH> <G> <E> <CR>

Where <HHHH> is repeated for each detector in detector order (0–2) as outlined by <D> above and is the signal in millivolts. This signal is in millivolts and offset by 4500 millivolts where 0=−4500 millivolts, 4500=0 millivolts, and 9000=+4500 millivolts The reference signal is always included and is the last signal transmitted in the message. <G> Gain and <E> Error are repeated for each detector and are decoded as follows (<E> is bit mapped messages once converted to binary):

Gain:
0-Gain Level 0
1-Gain Level 1
2-Gain Level 2
3-Gain Level 3

Error:
0-No Error
1-Signal Overload
2-Phase Change Timeout
4-ADC Conversion Timeout
8-Signal Acquisition Timeout

5.1.2 02-Measure Detector(s) Voltage at New Gain Level

Host Message Content:
<ESC> <M> <02> <D> <M> <G> <CR>
<D>-is defined as in message subtype 01.
<M>-Measurement mode:
0-Fast Mode
1-Slow Mode
2-Current Mode.

Both Fast Mode and Slow mode will provide a one-time override of the current measurement mode to make the signal acquisition.

<G>-New Gain value, which can be set for detectors 0–2 and which must be repeated in the message for each detector bit-mapped into the <D> parameter.

0-Gain Index 0
1-Gain Index 1
2-Gain Index 2
3-Gain Index 3

This will set the detector's current gain index level to this gain index. The Measurement head returns with a head 02 message as:

<ESC> <M> <02> <D> <HHHH> <G> <E> <CR>

The content of this message is identical to the content of the subtype 01 message described above.

5.1.3 03-Measure Detector(s) Voltage
Host Message Content:
<ESC> <M> <03> <D> <CR>

This message causes the measurement head to acquire the voltages for each detector bit-mapped by the <D> parameter. This message allows the measurement head to change gain levels (if required) To achieve good signal acquisition. The host must wait for the head to respond before continuing. The head will wait the signal acquisition timeout time if there are problems acquiring the signal, and then report back to the host with the error flag set for signal acquisition timeout.

The measurement mode (FAST/SLOW) is governed by the current data acquisition measurement mode in the head (no overrides are done).

The format of the message transmitted back to the host computer is:

<ESC> <M> <03> <D> <HHHH> <G> <E> <CR>.

The content of this message is identical to the content of the subtype 01 message described above.

5.1.4 04-Measure Temperature(s) Voltage
Host Message Content:
<ESC> <M> <04> <T> <CR>

This message causes the measurement head to acquire the temperature readings from each thermistor as mapped by the thermistor specifier value <T> as voltages. The thermistor mapping is as follows:
<T> is:
  1-Thermistor 0
  2-Thermistor 1
  3-Thermistor 0 & 1
  4-Thermistor 2
  5-Thermistor 0 & 2
  6-Thermistor 1 & 2
  7-Thermistor 0, 1, & 2
  8-Thermistor 3
  9-Thermistor 3 & 0
  A-Thermistor 3 & 1
  B-Thermistor 3, 0, & 1
  C-Thermistor 3 & 2
  D-Thermistor 3, 2, and 0
  E-Thermistor 3, 2, and 1
  F-Thermistor 3, 2, 1, and 0.

The measurement head will respond with a message in the following format once the measurement(s) is complete.

<ESC> <M> <04> <T> <HHHH> <E> <CR>

Where <HHHH> is repeated for each thermistor (lowest Thermistor index to highest Thermistor index) as outlined by <T> above and is the signal in millivolts. This signal is in millivolts and offset by 4500 millivolts where 0=−4500 millivolts, 4500=0 millivolts, and 9000=+4500 millivolts. <E> Error is repeated for each thermistor as outlined by <T> and is decoded as follows (bit mapped messages once converted to binary):
  0-No Error 5.1.5 05-Measure Temperature(s) In Degrees Centigrade
Host Message Content:
<ESC> <M> <05> <T> <CR>

This message causes the measurement head to acquire the temperature readings from each thermistor as mapped by the thermistor specifier value <T> as degrees C. The thermistor mapping is as described in submessage 04.

The measurement head will respond with a message in the following format once the measurement(s) is complete.

<ESC> <M> <05> <T> <HHHH> <E> <CR>

Where <HHHH> is repeated for each thermistor as outlined by <T> above and is the temperature in hundredths of degrees centigrade. The signal is offset by 80 degrees centigrade (8000 decimal) to provide a typical scan of ±80° C. (0=−80.00° C., 8000=1F40H=0° C., 16000=3E80H=80.00° C.). <E> Error is repeated for each thermistor as outlined by <T> and is decoded as follows (bit mapped messages once converted to binary):
  0-No Error 5.1.6 06-Measure Detector(s) Powers At Current Gain Level
Host Message Content:
<ESC> <M> <06> <D> <CR>
Where <D> is as detailed in submessage 01.

The measurement head responds with an <M> <06> message once the measurement is complete. The Measurement Head message content is:
<ESC> <M> <06> <D> <±> <M.MM> <E> <±> <ee> <G> <E> <CR>

Where <±M.MME±ee> is a floating point value representing the detector signal converted to power as:
  ±M.MME±ee <G> is the current gain level that the measurement was taken at and <E> is the error status. The floating point number, <G> and <E> are included in the response message, in detector order (0–2) for each detector desired by <D> sent to the measurement head. The reference power is always included and is the last signal transmitted in the message. The reference signal's power is converted based on the nominal reference voltage and the nominal reference power, while the signal powers are converted based on the detector's nominal responsivity and the responsivity temperature correction, if temperature correction is ON. The gain level <G> and the error status <E> are decoded as detailed in submessage 01.

5.1.7 07-Measure Detector(s) Powers At New Gain Level
Host Message Content:
<ESC> <M> <07> <D> <M> <G> <CR>
<D>-is defined as in message subtype 01.
<M>-Measurement mode as defined in message subtype 02.
Both Fast Mode and Slow mode will provide a one-time override of the current measurement mode to make the signal acquisition.
<G>-Gain Level, which can be set for detectors 0–2 and which must be repeated in the message for each detector that is bit-mapped into the <D> parameter. <G> is as defined in message subtype 02. The <G> parameter will set the detector's current gain index level to this gain index.

The Measurement head returns with a head 07 message as:

<ESC> <M> <07> <D> <±> <M.MM> <E> <±> <ee> <G> <E> <CR>

The content of this message is identical to the content of the subtype 06 message described above.

5.1.8 08-Measure Detector(s) Power
Host Message Content:
<:ESC> <M> <08> <D> <CR>

This message causes the measurement head to acquire the voltages for each detector bit-mapped by the <D> parameter. This message allows the measurement head to change gain levels (if required) to achieve good signal acquisition. The host must wait for the head to respond before continuing. The head will wait the signal acquisition timeout time if there are problems acquiring the signal, and then report back to the host with the error flag set for signal acquisition timeout.

The measurement mode (FAST/SLOW) is governed by the current data acquisition measurement mode in the head (no overrides are done).

The format of the message transmitted back to the host computer is:
<ESC> <M> <08> <D> <±> <M.MM> <E> <±> <ee> <G> <E> <CR>.

The content of this message is identical to the content of the subtype 06 message described above.

5.1.9 09-Measure Delta Absorbance
Host Message Content:
<ESC> <M> <09> <CR>
Head Response Message:
<ESC> <M> <09> <±> <M.MM> <±> <ee> <E> <CR>

Where E is (multiplexed for each detector) as described in message subtype 01.

5.1.10 10-Measure Contamination Level
Host message content:
<ESC> <M> <10> <CR>
Head response message:
<ESC> <M> <10> <±> <M.MM> <E> <1> <ee> <1> <CR>
where <I> is φ for no error, non-zero for an error.
The number represented by
±M.MM±ee
is the contamination level as converted from Delta absorbance as specified by the conversion factor in 3.1.24.

5.1.11 11-Acquire Reference Voltage & Gain Level
Host Message Content:
<ESC> <M> <11> <A> <HHHHHH> <CR>

This message causes the measurement head to enter a reference voltage signal acquisition mode. In this mode, the measurement head will increase reference gains until the reference voltage is at 85% of the maximum ADC value. Once this voltage has been acquired, the reference gain level and the nominal voltage (in millivolts) are transmitted back to the host.

Now, the parameters listed in the host message are:
<A>-Reference Acquisition State
  0-Acquire the reference voltage
  1-Abort the reference voltage acquisition.
  2-Report Current Reference Acquisition Status
<HHHHHH>-Reference Signal Acquisition Timeout Time in milliseconds. This is the amount of time that the measurement head should wait while acquiring the reference signal before a timeout occurs.

The head will immediately respond back to the host will an <M> <11> response message. The head may have to wait to acquire the reference, in which case the head will respond with a wait message. The host then must reinquire utilizing Reference Acquisition State <A>=2 to get the new status until the status is complete. If, at any time, the host computer desires to abort the acquisition before the timeout has occurred, a message with the reference acquisition state set to <A>=1 may be sent, at which time the head will respond with a reference signal acquisition aborted message.

The response message from the head is as follows:
<ESC> <M> <11> <A> <G> <HHHH> <CR>
Where <A> is:
  0-Reference voltage acquisition complete
  1-Reference voltage acquisition in progress (wait . . .)
  2-Reference voltage acquisition canceled
<G> is the desired gain index for the reference signal.
<HHHH> is a 4 digit hex number representing the nominal reference signal in millivolts.

Note that <G> and <HHHH> are only updated if <A> is 0.

After this message is received from the head, the values of <G> and <HHHH> are not used by the head until set with a <C> <12> and <C> <14> message.

What is claimed and desired to be secured by United States Letters Patent is:

1. A system for characterizing a rough, metallic surface, comprising:
  a light source capable of generating an incident beam of light;
  means for directing the incident beam of light onto the surface to produce reflected light;
  an optical filter arrangement configured to separate light into at least a first set of wavelengths which includes a target wavelength band, a second set of wavelengths which includes a first reference wavelength band outside the target band and a third set of wavelengths which includes a second reference band outside the target band and on the opposite side of the target band as the first reference band;
  means for directing a component of the reflected light into said optical filter arrangement;
  a first detector capable of detecting the intensity of light at the target band and of generating a signal corresponding to the detected intensity;
  means for directing the first set of wavelengths of received light into said first detector;
  a second detector capable of detecting the intensity of light at the first reference band and of generating a signal corresponding to the detected intensity;
  a third detector capable of detecting the intensity of light at the second reference band and of generating a signal corresponding to the detected intensity;
  means for directing the second set of wavelengths of received light into said second detector;
  means for directing the third set of wavelengths of received light into said third detector, and
  a signal processor in communication with said first and said second detectors for processing the signal generated by said first and said second detectors.

2. A system for characterizing a rough, metallic surface as defined in claim 1, further comprising a source detector capable of detecting the intensity of the incident beam of light and generating a signal corresponding to the detected intensity.

3. A system for characterizing a rough, metallic surface as defined in claim 2, further comprising means for modulating the incident beam such that the effect of any ambient light is substantially eliminated.

4. A system for characterizing a rough, metallic surface as defined in claim 1, wherein said means for directing the incident beam of light onto the surface to produce reflected light comprises a lens capable of focusing the incident beam at a discrete location on the surface.

5. A system for characterizing a rough, metallic surface as defined in claim 1, wherein said means for directing a component of the reflected light into said optical filter arrangement is configured to direct at least a portion of the back-scatter component of the reflected light.

6. A system for characterizing a rough, metallic surface as defined in claim 1, further comprising a scanning apparatus configured to change the point on the surface at which the incident beam of light is directed, thereby permitting the inspection of various discrete locations on the surface.

7. A system for characterizing a rough, metallic surface as defined in claim 6, further comprising communication means connecting said signal processor to said scanning apparatus such that the change of the point on the surface at which the beam of light is directed at the surface is capable of being synchronized with the processing of the signal generated by said detectors.

8. A system for characterizing a rough, metallic surface as defined in claim 7, further comprising an output device in communication with said signal processor for displaying data processed by said signal processor.

9. A system for characterizing a rough, metallic surface as defined in claim 1, further comprising at least one calibration plate having at least one contaminant of known thickness on its surface.

10. A system for characterizing a rough, metallic surface, comprising:
a light source capable of generating an incident beam of light;
means for directing the incident beam of light onto the surface to produce reflected light;
an optical filter arrangement comprising:
a first optical filter configured to reflect light corresponding to a first set of wavelengths while passing all remaining wavelengths of light; and
a second optical filter configured to reflect light corresponding to a second set of wavelengths while passing all remaining received light, said optical filter arrangement further configured such that the light received by said optical filter arrangement is separated into three beams which each correspond to a different set of wavelengths, wherein one of said beams includes a target wavelength band, wherein the second of said beams includes a first wavelength reference band outside of the target band and wherein the third of said beams includes a second wavelength reference band outside of the target band and on the opposite side of the target band as the first reference band;
means for directing a component of the reflected light into said optical filter arrangement;
a first detector capable of detecting the intensity of light at the target band and of generating a signal corresponding to the detected intensity;
a second detector capable of detecting the intensity of light at the first reference band and of generating a signal corresponding to the detected intensity;
a third detector capable of detecting the intensity of light at the second reference band and of generating a signal corresponding to the detected intensity;
means for directing the three beams of light separated by said optical filter arrangement into the detector corresponding to the set of wavelengths of the beam; and
a signal processor in communication with said detectors for processing the signal generated by said detectors.

11. A system for characterizing a rough, metallic surface as defined in claim 10, further comprising a source detector capable of detecting the intensity of the incident beam of light and generating a signal corresponding to the detected intensity.

12. A system for characterizing a rough, metallic surface as defined in claim 11, further comprising a chopper wheel for modulating the incident beam such that the effect of any ambient light is substantially eliminated.

13. A system for characterizing a rough, metallic surface as defined in claim 10, wherein said means for directing a component of the reflected light into said optical filter arrangement is configured to direct at least a portion of the back-scatter component of the reflected light.

14. A system for characterizing a rough, metallic surface as defined in claim 10, further comprising a scanning apparatus configured to change the point on the surface at which the incident beam of light is directed, thereby permitting the inspection of various discrete locations on the surface.

15. A system for characterizing a rough, metallic surface as defined in claim 14, further comprising communication means connecting said signal processor to said scanning apparatus such that the change of the point on the surface at which the beam of light is directed at the surface is capable of being synchronized with the processing of the signal generated by said detectors.

16. A system for characterizing a rough, metallic surface as defined in claim 15, further comprising an output device in communication with said signal processor for displaying data processed by said signal processor.

17. A system for characterizing a rough, metallic surface as defined in claim 10, further comprising a temperature sensor in communication with at least one of said detectors.

18. A system for inspecting a rough, metallic surface for the presence of a hydrocarbon contaminant, comprising:
an infrared light source capable of generating an incident beam of light;
a lens for directing the incident beam of light onto the surface, said lens positioned such that the incident beam is directed at the surface at an angle of incidence of about 45 degrees, thereby producing reflected light;
an optical filter arrangement configured for receiving a portion of the back-scatter component of the reflected light, said optical filter arrangement comprising:
- a first high-pass filter configured to reflect light having a wavelength less than about 3.3 microns while passing all remaining wavelengths of light;
- a first band-pass filter positioned to receive the light passed by said first high-pass filter, said first band-pass filter configured to pass light having a wavelength of from about 3.65 microns to about 3.75 microns while reflecting all remaining wavelengths of light;
- a second band-pass filter positioned to receive the light reflected by said first high-pass filter, said second band-pass filter configured to pass light having a wavelength of from about 3.15 microns to about 3.25 microns; and
- a third band-pass filter positioned to receive the light reflected by said first band-pass filter, said third band-pass filter configured to pass light having a wavelength of from about 3.35 microns to about 3.45 microns;
- a first detector positioned to receive the light reflected from said first high-pass filter and through said second band-pass filter, said first detector capable of detecting the intensity of light and of generating a signal corresponding to the intensity of the received light;
- a second detector positioned to receive the light reflected from said first band-pass filter and through said third band-pass filter, said second detector capable of detecting the intensity of light and of generating a signal corresponding to the intensity of the received light;
- a third detector positioned to receive the light passed by said first band-pass filter, said third detector capable of detecting the intensity of light and of generating a signal corresponding to the intensity of the received light;
- a signal processor in communication with said detectors for processing the signal generated by said detectors;
- a scanning apparatus configured to change the point on the surface at which the incident beam of light is directed, thereby permitting the inspection of various discrete locations on the surface; and
- an output device in communication with said signal processor for displaying data processed by said signal processor.

19. A system for inspecting a rough, metallic surface as defined in claim 18, further comprising a source detector capable of detecting the intensity of the incident beam of light and generating a signal corresponding to the intensity of the incident beam.

20. A system for inspecting a rough, metallic surface as defined in claim 19, further comprising a chopper wheel for modulating the incident beam such that the effect of any ambient light is substantially eliminated.

21. A system for inspecting a rough, metallic surface as defined in claim 18, further comprising a temperature sensor in communication with at least one of said detectors.

22. A process for characterizing a rough, metallic surface, comprising the steps of:
- directing an incident beam of light onto a discrete location on the surface to be inspected;
- gathering at least a portion of the light reflected off the surface;
- introducing the gathered portion of the reflected light into an optical filter arrangement configured to separate the gathered portion of the reflected light into at least a first set of wavelengths which includes a target wavelength band, a second set of wavelengths which includes a first reference wavelength band outside the target band and a third set of wavelengths which includes a second reference wavelength band outside the target band and on the opposite side of the target band as the first reference band;
- monitoring the intensity of the gathered portion of the reflected light at the target band and at the first and second reference bands by directing the first set of wavelengths into a first detector capable of detecting the intensity of light at the target band and of producing a signal corresponding to the detected intensity, directing the second set of wavelengths into a second detector capable of detecting the intensity of light at the first reference band and of producing a signal corresponding to the detected intensity and directing the third set of wavelengths into a third detector capable of detecting the intensity of light at the second reference band and of producing a signal corresponding to the detected intensity; and
- analyzing the signals produced by the detectors to characterize the surface.

23. A process for characterizing a rough, metallic surface as defined in claim 22, wherein said introducing step comprises introducing the gathered portion of the reflected light into a first optical filter configured to reflect light generally corresponding to the second set of wavelengths while passing all remaining wavelengths of light and introducing the light passed by the first optical filter into a second optical filter configured to reflect light corresponding to the first set of wavelengths while passing all remaining received light.

24. A process for characterizing a rough, metallic surface as defined in claim 22, wherein the step of directing an incident beam of light onto a discrete location on the surface to be inspected comprises directing the incident beam of light at an approximate 45 degree angle to the surface.

25. A process for characterizing a rough, metallic surface as defined in claim 22, wherein said analyzing step is followed by the step of redirecting the beam of light onto a different discrete location on the surface to be inspected and repeating the preceding steps, whereby representative locations on the surface are inspected.

26. A process for characterizing a rough, metallic surface as defined in claim 22, wherein said gathering step includes gathering at least a portion of the backscatter component of the reflected light.

27. A process for characterizing a rough, metallic surface as defined in claim 26, wherein the surface is a one-dimensionally rough surface and said directing step includes directing the beam onto the surface at a direction perpendicular to the lines which comprise the surface roughness.

28. A process for characterizing a rough, metallic surface as defined in claim 22, further comprising the step of detecting the intensity of the incident beam of light with a source detector, generating a signal corresponding to the intensity of the incident beam and normalizing the signals produced by the first, second and third detectors to reduce the effect of fluctuations in the intensity of the incident beam of light.

29. A process for characterizing a rough, metallic surface as defined in claim 28, further comprising the step of substantially eliminating the effect of ambient light by modulating the incident beam with a chopper wheel.

30. A process for characterizing a rough, metallic surface as defined in claim 22, further comprising the step of monitoring the temperature of at least one of the detectors and adjusting the signals produced by the detectors to reduce the effect of fluctuations in the temperature of the detectors.

31. A process for characterizing a rough, metallic surface as defined in claim 22, wherein said analyzing step includes processing the signal produced by the detectors with a computer.

32. A process for characterizing a rough, metallic surface as defined in claim 31, wherein the step of processing the signal produced by the detectors is synchronized with the step of redirecting the beam of light onto a different location on the surface to be inspected.

33. A process for characterizing a rough, metallic surface as defined in claim 22, wherein said monitoring step includes monitoring the intensity of light at a target band of about eight microns to thereby characterize a silicone release agent.

34. A process for characterizing a rough, metallic surface as defined in claim 22, wherein said monitoring step includes monitoring the intensity of light at a target band of from about three to about four microns to thereby characterize a hydrocarbon.

35. A process for characterizing a rough, metallic surface as defined in claim 22, wherein said directing step includes focusing the beam onto a discrete location on the surface with a lens.

36. A process for characterizing a rough, metallic surface as defined in claim 22, wherein said directing step is preceded by calibrating the system with at least one calibration plate having at least one contaminant of known thickness on its surface.

37. A process for characterizing a rough, metallic surface as defined in claim 36, wherein said analyzing step further includes determining the thickness of the contamination.

38. A process for characterizing a rough, metallic surface as defined in claim 37, wherein said identifying step further includes displaying a color scale image corresponding to the thickness of the contamination.

39. A process for characterizing a rough, metallic surface as defined in claim 37, wherein said identifying step further includes displaying a surface map of the contamination.

* * * * *